United States Patent [19]
Jones et al.

[11] Patent Number: 5,306,909
[45] Date of Patent: Apr. 26, 1994

[54] ANALYSIS OF DRILLING FLUIDS

[75] Inventors: Timothy Jones, Cottenham; Trevor Hughes, Cherry Hinton; Patrick Tomkins, Chesterton, all of England

[73] Assignee: Schlumberger Technology Corporation, Houston, Tex.

[21] Appl. No.: 860,879

[22] Filed: Mar. 31, 1992

[30] Foreign Application Priority Data

Apr. 4, 1991 [GB] United Kingdom ............... 9107041

[51] Int. Cl.$^5$ ..................... G01V 9/04; G01N 21/35
[52] U.S. Cl. .................................. 250/255; 250/256; 250/339.01
[58] Field of Search ................. 175/41, 48, 207; 250/339, 255, 256; 378/45, 47

[56] References Cited

U.S. PATENT DOCUMENTS

| | | | |
|---|---|---|---|
| 4,321,465 | 3/1982 | Stover et al. | 250/255 |
| 4,608,859 | 9/1986 | Rockley | 73/153 |
| 4,609,821 | 9/1986 | Summers | 250/255 |
| 4,620,284 | 10/1986 | Schnell et al. | 356/301 |
| 4,635,735 | 1/1987 | Crownover | 175/48 |
| 4,800,279 | 1/1989 | Hieftje et al. | 250/339 |
| 4,839,516 | 6/1989 | Freeman et al. | 250/255 |
| 4,878,382 | 11/1989 | Jones et al. | 73/153 |
| 4,994,671 | 2/1991 | Safinya et al. | 250/339 |
| 4,996,421 | 2/1991 | Rai et al. | 250/255 |
| 5,084,617 | 1/1992 | Gergely | 250/255 |

FOREIGN PATENT DOCUMENTS

| | | |
|---|---|---|
| 0461321A | 12/1991 | European Pat. Off. |
| 1254144A | 8/1986 | U.S.S.R. |
| 1516907A | 10/1989 | U.S.S.R. |
| 2217838A | 11/1989 | United Kingdom |
| 2237303A | 5/1991 | United Kingdom |
| 2237304A | 5/1991 | United Kingdom |
| 2237305A | 5/1991 | United Kingdom |

OTHER PUBLICATIONS

Applied Spectroscopy, vol. 42, No. 2, 1988, pp. 228-236, M. P. Fuller, G. L. Ritter and C. S. Draper, "Partial Least-Squares Quantitative Analysis of Infrared Spectroscopic Data. Part II: Application to Detergent Analysis".

Chemical, Biological and Industrial Applications of Infrared Spectroscopy, John Wiley & Sons, pp. 111-128 (Brown & Elliot).

Trends in Analytical Chemistry, vol. 7, No. 5, May 1988 pp. 164 et seq, Leyden et al, "Diffuse Reflectance Fourier Transform IR Spectroscopy".

Applied Spectroscopy, vol. 34, No. 5, 1980, pp. 533-539, Haaland et al., "Improved Sensitivity of Infrared Spectroscopy by the Application of Least Squares Methods".

The Oil Weekly, Aug. 1, 1938, pp. 18-20, "Continuous Determination of Oil and Gas Content of Drilling Mud Helpful".

Primary Examiner—Carolyn E. Fields
Attorney, Agent, or Firm—John J. Ryberg; Wayne I. Kanak

[57] ABSTRACT

A method of quantitative analysis of drilling fluids comprising subjecting an untreated wet sample of the fluid to a reflectance infrared spectroscopy technique, typically attenuated total reflectance spectroscopy, and comparing the spectrum obtained with spectra obtained from calibration samples of fluids of known composition. The sample can be obtained directly from the flowing mud with no preparation or alternatively the sample might comprise a prepared sample which is re-suspended in a liquid phase carrier. The sample can also be analysed for non-spectral properties which might also provide useful information in conjunction with spectral data. The method requires little or no sample preparation and can be used to quantitatively analyse both water-based and oil-based drilling fluids using a continuous in-line and/or on-line arrangement.

12 Claims, 35 Drawing Sheets

ANALYSIS OF DRILLING FLUIDS

BACKGROUND OF THE INVENTION

1. Field of the Invention

This invention concerns the analysis of drilling fluids (usually called "mud") used to drill a well.

2. Description of Related Art

In the rotary drilling of wells, such as hydrocarbon wells, a drilling fluid or mud is continuously circulated from the surface down to the bottom of the hole being drilled and back to the surface again. The mud has several functions, one of them being to transport cuttings drilled by the drill bit up to the surface where they are separated from the mud, while another is to impose an hydrostatic pressure on the walls of the borehole so as to avoid a collapse of the borehole and an influx of gas or liquid from the formations being drilled. The characteristics of the mud are therefore important to monitor and to keep within certain limits. For instance, the viscosity of the mud is an important characteristic since it contributes to the cuttings transport capability of the mud. Clays, such as bentonite clay, are added to the mud so as to keep the drilled cuttings in suspension as they move up the hole (the clay also sheathes the wall of the hole; this thin layer of clay, called filter cake, reduces the loss of mud to permeable formations caused by filtration). The density of the mud is another significant factor. It must be large enough so as to exert a certain hydrostatic pressure on the formation, but not too large to fracture these formations. Weighting materials, barite for example, are added to the mud to make it exert as much pressure as needed to contain the formation pressures. These are examples of the numerous chemicals available to give the mud the exact properties it needs to make it as easy as possible to drill the hole.

Drilling muds are of two main types, distinguished by whether water or oil is used as the continuous phase. Water-based muds are typically suspensions of bentonite clay, to which further heavier minerals (usually barite), polymers and surfactants are added to optimise the rheology and other physical properties for a particular job. Oil-base drilling fluids, on the other hand, are most commonly water-in-oil emulsions where micron-sized brine droplets, stabilised by emulsifier, are dispersed in a mineral oil, along with organophilic clays, weighting minerals, wetting agents and oil-soluble viscosifiers.

In addition to the products deliberately added in the drilling mud for specific purposes, other materials coming from the formation being drilled and/or from the borehole wall can be present in the mud. These products are mainly in the form of minute particles of solids (an average diameter being about 50–100 microns), and are usually called "fines". Examples of "fines" are silica (quartz), carbonates, and dispersed clay particles.

As noted above, one of the mud's functions is to transport the drilled cuttings up to the surface. The cuttings are then separated off using solids control equipment, and the mud, possibly after the addition of one or more materials to restore its make-up and properties, is re-used.

A number of solids control devices are used to remove drilled cuttings and solids from the return mud. The cuttings, which typically have a particle size between several millimeters and about 175 microns, are filtered from the return mud using vibrating screens known as "shale shakers". Sand-sized drilled solids (which have particle sizes in excess of about 75 microns) and silt-sized drilled solids (which have particle sizes in excess of about 2 microns) are removed by hydrocyclone demanders and hydrocyclone desilters respectively. Under certain circumstances, decanting centrifuges may also be used to remove fine drilled solids which have particle sizes less than 20 microns. A typical set-up for a solids control system is seen in FIG. 26 of the accompanying Drawings, which shows the main components of the mud circulation equipment. The mud (10) is contained in a mud pit (12), called the active tank. A pump (14) draws up the mud from the pit through a pipe (16), and forces the mud through the discharge line (18), the stand pipe (20), the rotary hose (22) and the swivel (24). The mud then flows into the kelly (26) and down the borehole (28) in the drill pipe (30) and the drill collars (32). The mud reaches the bottom of the hole at the drill bit (34), and then flows up to the surface in the annulus (36) and in the mud return line (38). The return mud, laden with drilled material, then falls over a vibrating screen-like device (40), called a shale shaker. Shale shaker underflow mud is fed (via line 44) to additional solids control equipment (42), which may include a combination of devices such as a degasser, hydrocyclone desander/desilter, and/or decanting centrifuges. Solids control equipment underflow mud is fed (via line 46) to the active tank 12. Batches of freshly prepared mud and quantities of mud products are added to the active tank mud 10 during drilling. The batches of freshly prepared mud replace (i) volumes of mud taken up by an increasing volume of borehole 28, (ii) volumes of mud lost on solids removal by the solids control equipment 40 and 42, and (iii) volumes of mud which may be discarded due to a loss of desired properties (such as mud containing large quantities of fine drilled solids which cannot be removed by the solids control equipment but which would slow down drilling if recirculated into the borehole). Quantities of mud products are added to mud in the active tank so as to maintain their concentration specified in the original mud formulation.

It will be readily apparent that in order to monitor the composition of the mud and drilled material during drilling, it is necessary to have results from accurate analysis not only of the mud but also of the solids separated therefrom by the various stages of the solids control equipment. So far as the latter are concerned, it should be borne in mind that, whilst the composition of the removed drilled cuttings and solids is typically dominated by mineral components originating from the rock formations being drilled, there will also be present considerable quantities of added mud product components coming from the mud formulation.

To give some idea of the scale of the problem it should be noted that typical field data indicate that approximately one liter of mud may be removed by the solids control equipment for every one liter of formation drilled. Therefore, in order to maintain a constant volume of mud in surface holding tanks, the mud engineer needs in principle to add two liters of fresh mud volume for every one liter of formation drilled (in practice, additional volumes of fresh mud may be added to replace return mud which is discarded due to its non-optimum properties). Current mud engineering practices do not attempt to evaluate and account for losses of mud products in solids removed by the solids control equipment or in discarded mud.

Investigations have also indicated that for every volume of dried cuttings produced by a typical shale shaker configuration an equal volume of mud is removed. Such a degree of "contamination" of cuttings by a typical barite-weighted mud formulation (with mud density, $p(m)=1.2$ kg/l and average mud solids density, $\rho_{(ms)}=4.1$ kg/l) used to drill a typical formation (with average formation density, $\rho_{(f)}=2.6$ kg/l) produces dried cuttings solids which contain 89.8 weight percent formation mineral components and 10.2 weight percent mud product components. And it is well known that considerable quantities of the coarser fractions of API-grade barite are present in solids removed by the hydrocyclones.

A variety of techniques are employed to determine the nature and amounts of the numerous components in the mud and the removed solids, but not all are equally satisfactory. Thus: the current field technique used to determine the solids content of a mud sample involves the use of a retort to dry the sample to constant weight. This technique measures percentage solids by volume and by weight, allowing an average solids density to be calculated; the latter data are used to calculate a percentage "high gravity solids" (assuming a high gravity solids density, $\rho_{(hgs)}=4.3$ kg/l) and a percentage of "low gravity solids" (assuming a low gravity solids density $\rho_{(lgs)}=2.5$ kg/l). Such a technique may also be applied to an analysis of solids removed by the solids control equipment, but here it can be highly inaccurate; for example, an apparently increasing high gravity fraction in solids removed by a hydrocyclone may in fact be caused by an increasing average formation density due to a change of drilled lithology. Further inaccuracies may be introduced as a result of varying concentrations of salt components originating from added mud products or, more particularly, when drilling through evaporate sequences.

The published and presently used methods for the analysis of drilled cuttings have focussed on a qualitative and/or quantitative assessment of mineral components in order to evaluate the composition of drilled lithologies. During a conventional mud logging operation, cuttings samples may be taken from the shale shaker after drilling intervals of 20-50 feet. Each cuttings sample is evaluated by a geologist who carries out a number of qualitative tests and provides a lithological description for the mud log. The technique most widely used in the industry for a quantitative determination of the mineral components in drilled cuttings and core samples is x-ray diffraction analysis (XRD). XRD is normally capable of quantifying minerals within a relative accuracy of ±5-10%; however, crystallinity differences between standards and unknown samples, and the presence of amorphous material (for example, organic material such as kerogen from the formation, or contaminant polymeric mud products), may introduce considerable systematic error.

Another method proposed for the quantitative analysis of mineral components in core samples and drilled cuttings is the subject of two recent U.S. Pat. Nos. (4,608,859 and 4,839,516), namely infrared spectroscopy (particularly Fourier-transform infrared spectroscopy, FTIR) in the wave number range 5,000 to 400 $cm^{-1}$ (2,000 to 25,000 nanometers), corresponding to mid-range infrared. The method described in the latter patent involves: (i) a cleaning procedure to remove components other than the analyte mineral components; (ii) the reduction of sample particle size to an average of one micron, with no particles larger than two microns; (iii) the dilution of the crushed sample with potassium bromide (KBr); (iv) the production of a pressed disc from which a transmission FTIR spectrum is obtained; and (v) a comparison of the sample spectrum with transmission spectra for pure minerals in order to obtain a quantitative mineralogical analysis. It is important to note that the method described states that any hydrocarbon in the core sample is removed by techniques such as toluene solvent extraction or $CO_2$ cleaning prior to the mineralogical analysis; the patent does not describe a method to determine the hydrocarbon content or the content of any component other than the mineral components in a core or cuttings sample.

The use of FTIR spectroscopy to determine mineral composition of rock samples, such as shale samples, has also been described in the article entitled *The quantitative analysis of complex multicomponent mixtures by FT-IR; the analysis of minerals and of interacting blends* by James M. Brown and James J. Elliott, published in the book *Chemical, Biological and Industrial Applications of Infrared Spectroscopy*, a Wiley-Interscience publication, 1985. The article proposes a method for the determination of minerals in rock samples which involves: (i) pregrinding the mineral to 325 mesh; (ii) dispersion of the ground mineral in KBr; (iii) the production of a pressed disc from which a transmission FTIR spectrum is obtained; and (iv) a comparison of the sample spectrum with transmission spectra for pure minerals in order to obtain a quantitative mineralogical analysis.

An alternative infrared analytical technique is the subject of GB Patent Specification No: 2,217,838 which is mainly concerned with the specific determination of oils and other materials, for which it can be advantageous to use the overtone and combination bands of the fundamental O-H, C—H and N—H stretching vibrations since this provides more information relating to chemical composition than the fundamental bands. However, the overtone and combination bands of the fundamental vibration frequencies of bands containing heavier atoms, commonly found in minerals (e.g. S—O, Si—O) and polymers (e.g. C—N, C—O) are predominantly found in the mid-infrared and therefore are not revealed. By opposition, these heavier materials are particularly well revealed by reflectance techniques described herein.

It will be evident that accurate evaluation of mud products provides information with which to compile a mass balance for the mud components on a regular basis. Such information may be used to account for the mud products during a mud engineering service. Regular mass balances for each mud product provide useful information with which both to evaluate and account for their losses in solids removed by the solids control equipment and to monitor the performance of mud products such as an encapsulating polymer. However, none of the analytical techniques presently in use allow this to be effected, for none accurately analyse the removed solids because they either ignore or incorrectly assess the mud products carried by these removed solids.

In addition, a major area of environmental concern is the retention of oil on drilled cuttings either when using an oil-based mud formulation or when lubricant oils are added to a water-based mud formulation. At present, there are no adequate analytical techniques to determine the oil content of solids removed by the solids control equipment at the rigsite, but one is required in order to provide, inter alia, the necessary information for an accurate accounting for the base or lubricant oil and in order to assess the environmental impact that a discharge of such cuttings would have on the near-rig environment (and the technique may also be applied to an assessment of the efficiency of the various cleaning processes which may be used to recover the oil from solids removed by the solids control equipment).

In our co-pending EPC Applications Nos: 90202795.2 and 90202796.0 there are described quantitative analysis methods for mud products, which methods use mid-. range infrared spectroscopy, most preferably Fourier-transform infrared spectroscopy carried out in reflectance mode on a raw, undiluted or diluted (in KBr) sample of dried and powdered mud solids and for drilled cuttings and other removed solid materials together with any mud products carried thereby.

The previously proposed techniques are only applicable to the analysis of mud products in water based muds and require extensive sample preparation. The techniques are not applicable to oil based muds since the temperature required to remove the water and sufficient oil to form a dry powder results in decomposition of organic mud products such as emulsifiers and organophilic clays. The previously proposed techniques are essentially batch techniques which may only be applicable to a relatively infrequent check on the composition of a water based mud, for example, for a check on the composition of input, output and drilled cuttings composition approximately five times per 24 hours of drilling. The techniques are not applicable to a continuous in-line and/or on-line measurement of mud composition.

The present invention has arisen in an attempt to provide a method for analysing drilling fluids which requires little or no sample preparation and which can be used to quantitatively analyse both water-based and oil-based drilling fluids using a continuous in-line and/or on-line arrangement.

SUMMARY OF THE INVENTION

In accordance e present invention, there is provided a method of quantitative analysis of a well fluid comprising solid or liquid components which are dispersed or dissolved in a liquid carrier, the method comprising: taking a sample of the fluid, recording the infra red spectrum of the sample and comparing the spectrum with a model in which the contribution of the components of the fluid to the spectrum is predicted in order to determine the composition of the fluid, characterised in that the sample includes the carrier liquid.

The present invention differs from those of the prior art in that a continuous liquid phase is present in the sample. Thus the sample can be obtained directly from the flowing mud with no preparation or alternatively the sample might comprise a prepared sample which is re-suspended in a liquid phase carrier. By performing the method on such a sample of fluid, the measurements can be considered as representative of measurement conducted on the drilling fluid in its normal state. This means that the same sample can be analysed for non-spectral properties which might also provide useful information in conjunction with spectral data.

The infrared analysis technique used is preferably attenuated total reflectance spectroscopy (ATR) although in certain circumstances, it is envisaged that diffuse reflectance techniques might also be used. Whichever technique is used, it is preferred that a Fourier transform infrared method should be used.

The mud sample analysed can be taken directly from the mud circulating system, either before or after any solids control equipment. Furthermore, solids removed in the solids control equipment can be subjected to such analysis, typically involving wet crushing of the components to a particle size of less than about 50 microns.

BRIEF DESCRIPTION OF THE DRAWINGS

The present invention will now be described with reference to various examples and drawings which show the following.

DESCRIPTION OF THE PREFERRED EMBODIMENTS

The present invention requires the use of a reflectance infrared spectrometry technique, attenuated total reflectance spectroscopy being preferred. The use of attenuated total reflectance (ATR) techniques in infrared spectrometry is well known; a review of the techniques can be found in N. J. Harrick, *Internal Reflection Spectroscopy*, Wiley-Interscience, New York (1967), and G. Kortüm, *Reflectance Spectroscopy*, Springer-Verlag, Berlin-Heidelberg (1969). The basis of the technique is to use the evanescent wave which propagates into the optically rarer medium from an optically denser medium under the condition of total internal reflection (see FIG. 1). The optically rarer material constitutes the sample for which the spectrum is required, while the optically denser material is a crystal characterised by both a high refractive index and a high transmissivity to infrared radiation. Typical materials used for ATR crystals are zinc selenide, sapphire and germanium.

Figure 1:
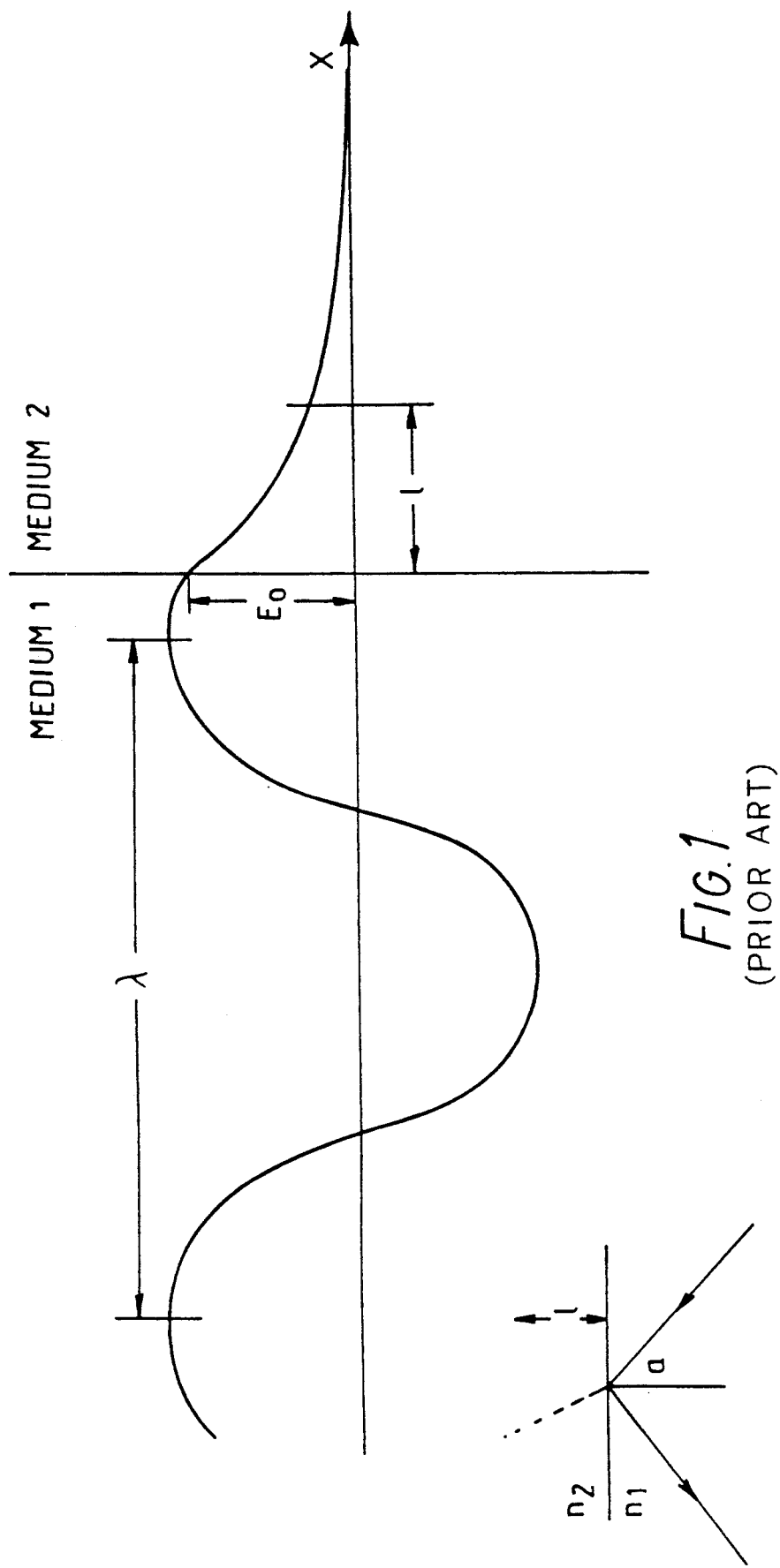
FIG. 1 Schematic representation of evanescent wave in optically rarer medium (medium 2) under condition of total internal reflection in optically denser medium (medium 1). Inset shows geometry of total internal reflection at crystal plate.

The attenuation of the radiation in the optically rarer medium (sample) can be described by $$E(X) = E_o \exp\left(-\frac{X}{l}\right) \quad [1]$$

where X is the distance of propagation into the optically rarer medium, $E_o$ is the electric vector at the interface in the optically denser medium, E(X) is the amplitude of the electric vector in the optically rarer medium and l is a characteristic penetration depth (FIG. 1). The penetration depth l is a characteristic of the optical geometry, the ATR crystal and the sample material. The characteristic penetration depth is given by $$l = \frac{\lambda}{2n_1\pi \sqrt{(\sin^2\alpha - (n_2/n_1)^2)}}, \quad [2]$$

where λ is the wavelength of the infrared radiation (typically 2.5-25 μm), α is the angle of incidence in the optically denser medium of refractive index $n_1$ and $n_2$ is the refractive index of the sample. A common configuration for an ATR cell is a zinc selenide crystal ($n_1$ = 2.43 at λ = 5 μm) with a 45° prism to give a value of α of 45°, for which equation [2] becomes $$l = \frac{\lambda}{15.3 \sqrt{(0.5 - (n_2/2.43)^2)}} \quad [3]$$

For a given ATR configuration, the penetration depth depends only on the wavelength of the radiation and the refractive index of the sample. For example, with water as the sample (average value of $n_2$ = 1.33), the depth of penetration is l≈λ/7 (0.4-4 μm). The total path length of the radiation in the sample is approximately Nl where N is the number of total internal reflections undergone by the infrared radiation in the ATR crystal.

In the following examples, spectra are taken from static or flowing samples. In the static case, a discrete sample is placed on the ATR plate and the spectrum recorded. For flowing measurements, the apparatus shown in FIG. 10 was used and the spectra recorded while the sample was being pumped through the ATR cell.

Figure 2:
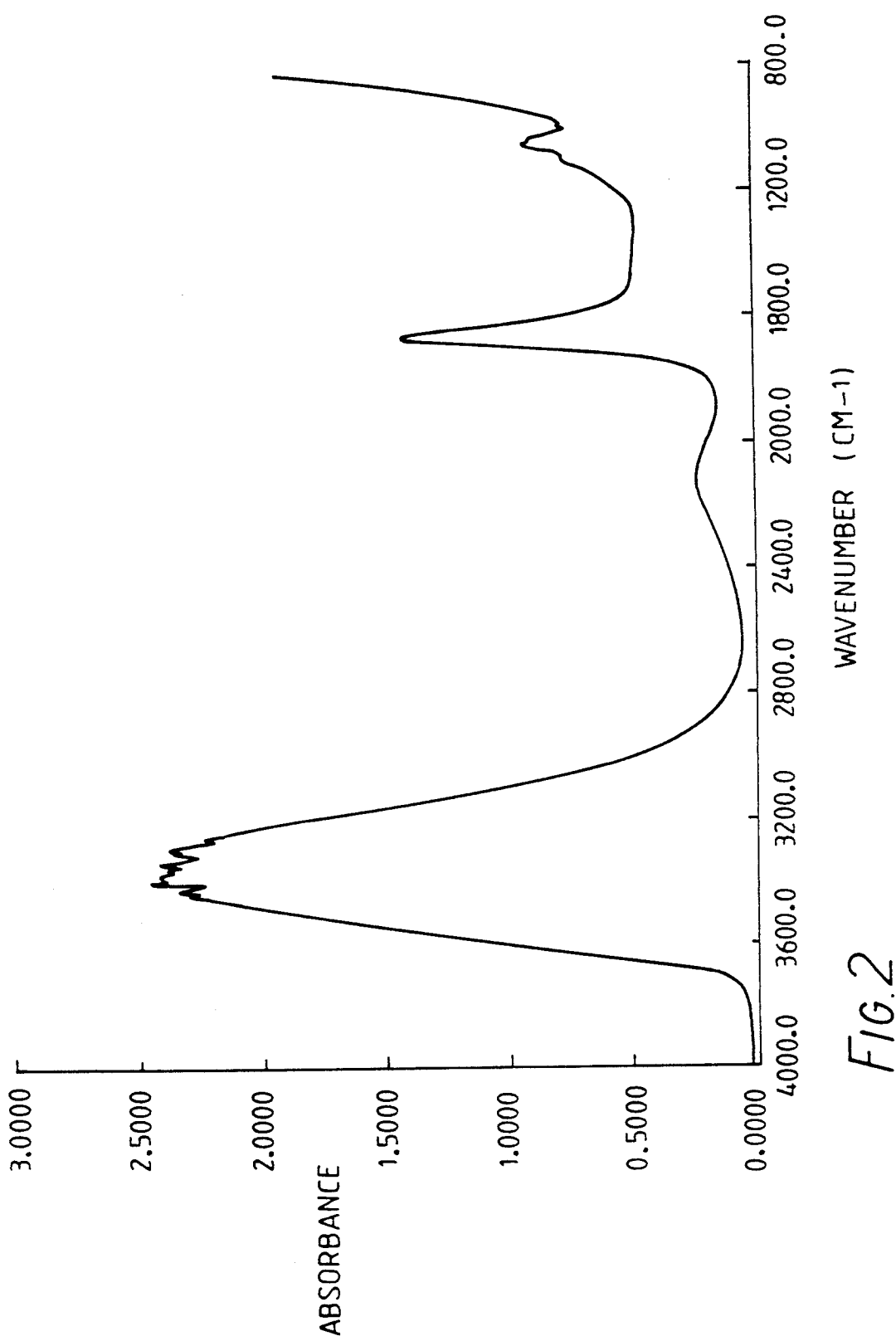
FIG. 2 Infrared spectrum of raw water-based drilling mud obtained with 45° zinc selenide ATR plate.
Figure 3:
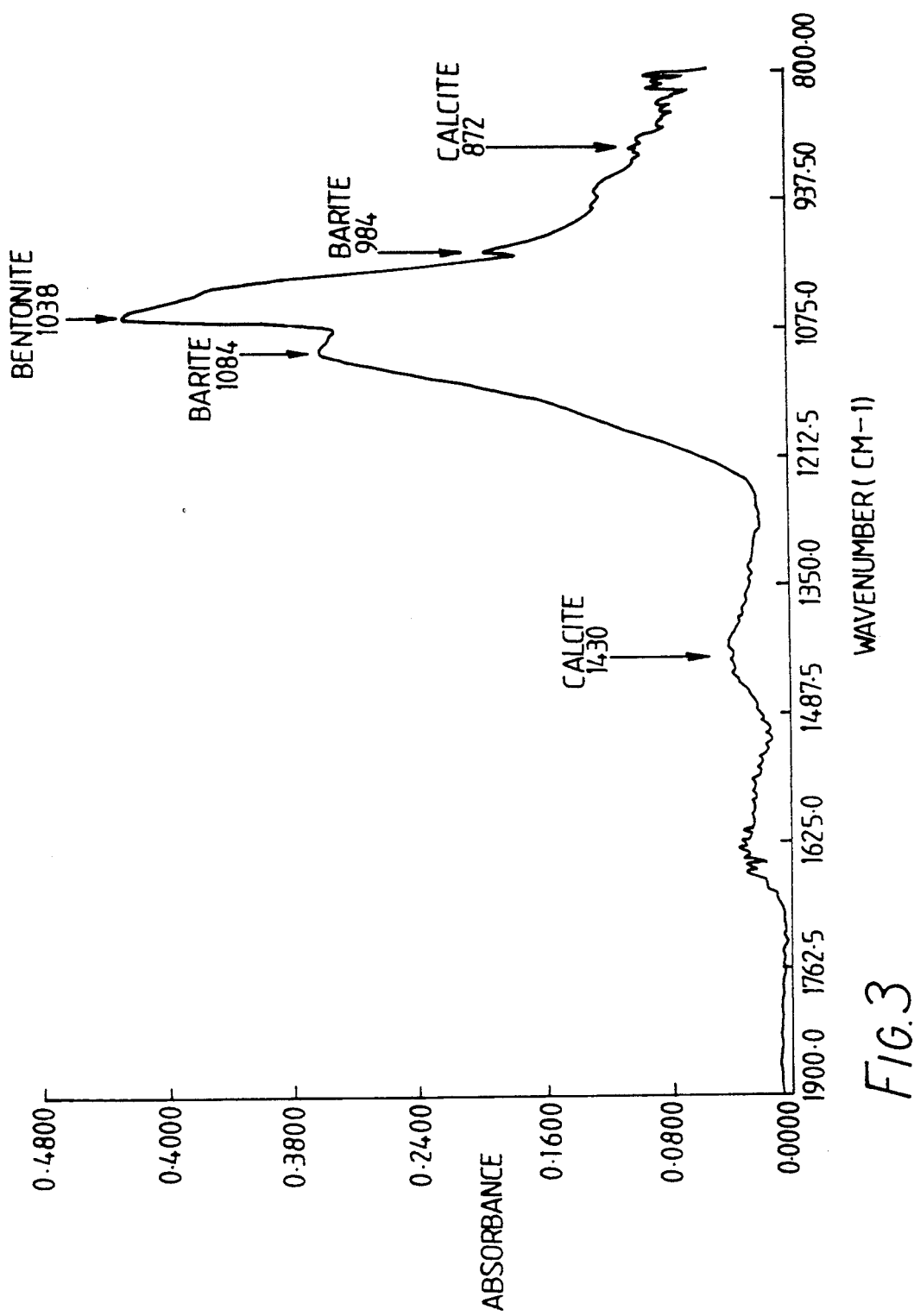
FIG. 3 Infrared spectrum of water-based drilling fluid (as shown in FIG. 2) with subtraction of 0.97 of water spectrum.
Figure 4:
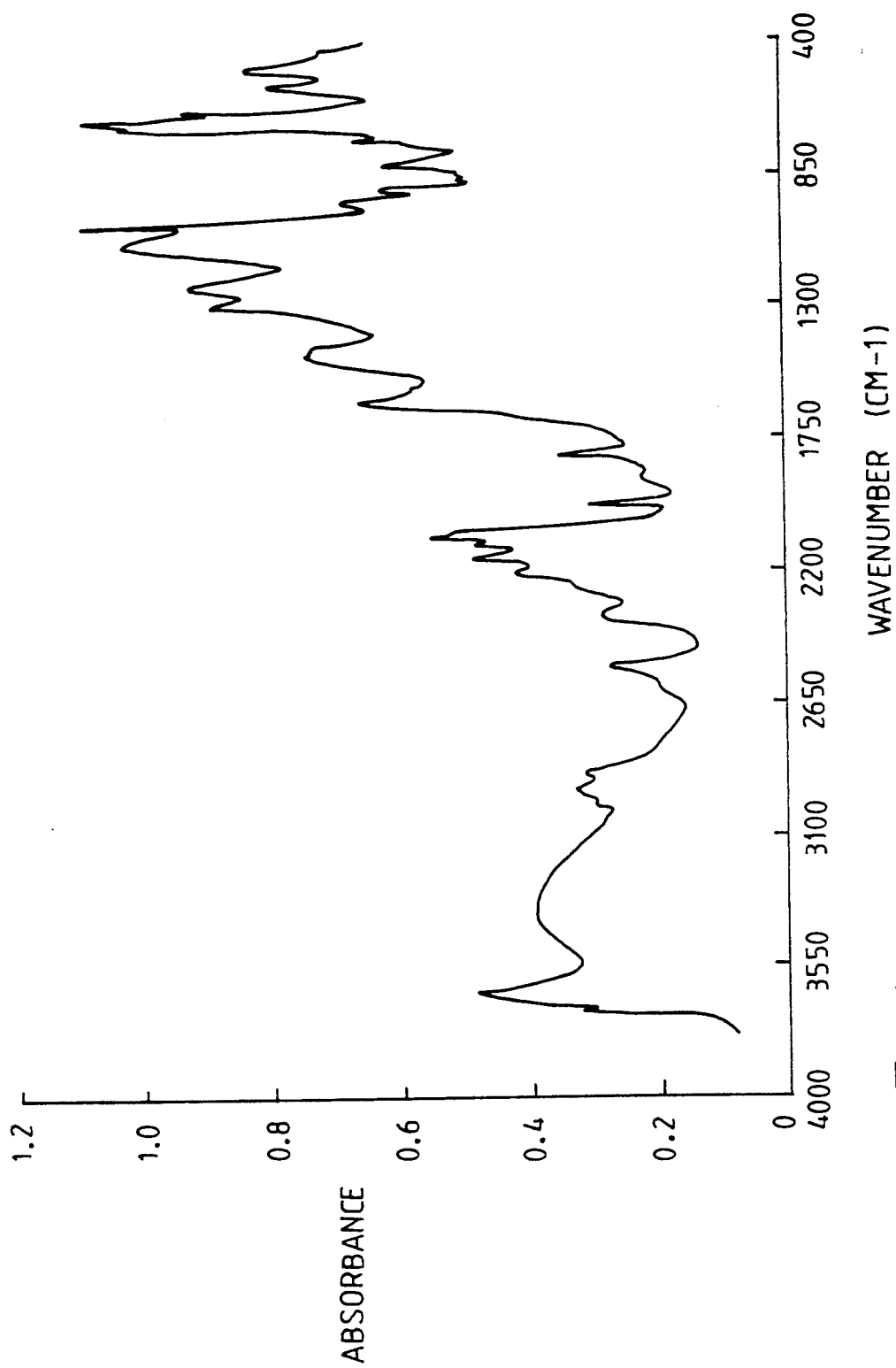
FIG. 4 Diffuse reflectance spectrum of dried mud solids and polymers obtained from water-based drilling fluid (liquid mud spectrum shown in FIG. 2)
Figure 5:
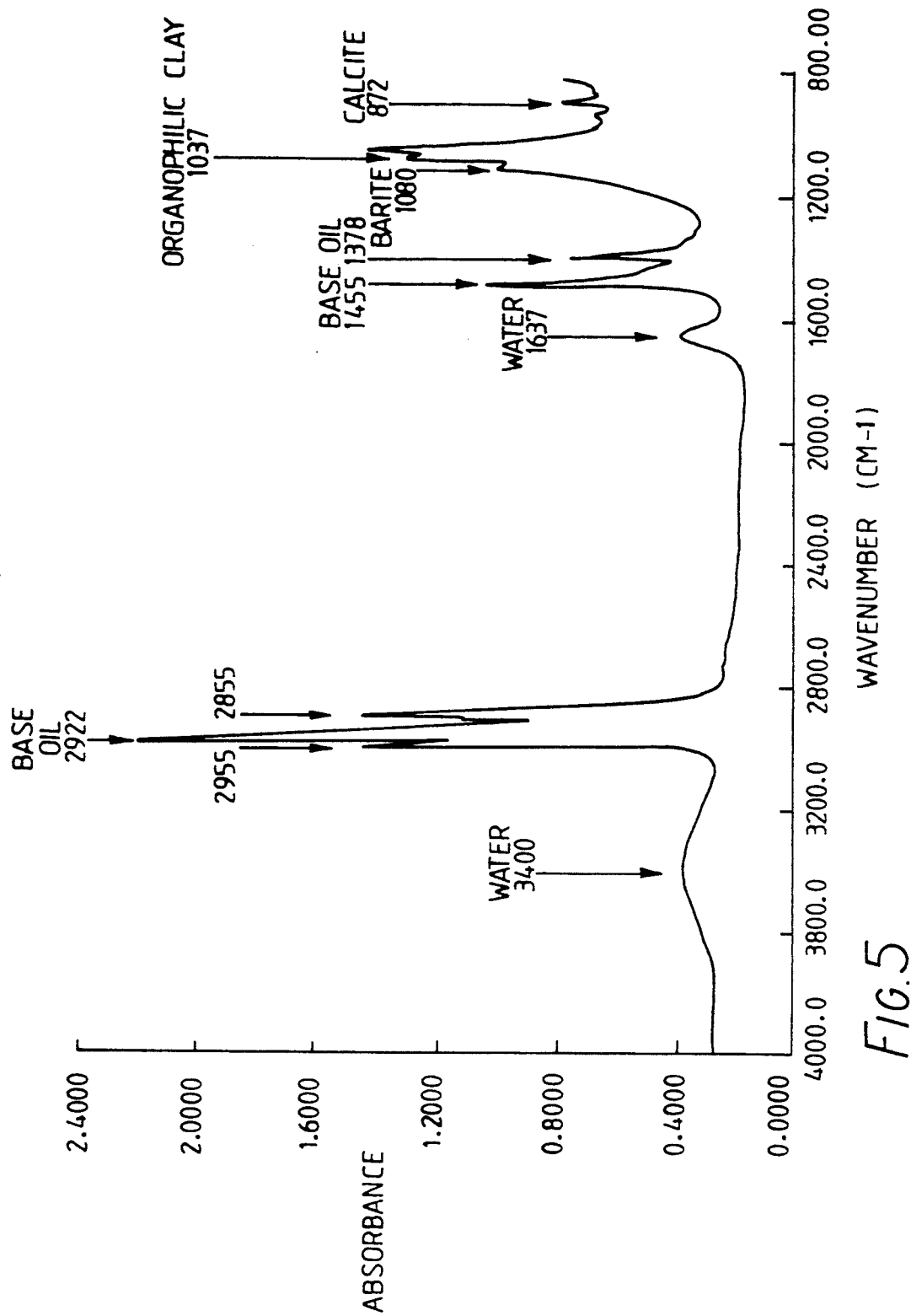
FIG. 5 Infrared spectrum of oil-based drilling fluid.

FIG. 2 shows the infrared spectrum of a water-based mud over the spectral region 4000-800 cm$^{-1}$ using an ATR sampling cell having the configuration defined above. There is strong absorption of the zinc selenide crystal below about 900 cm$^{-1}$. The spectrum is dominated by the presence of water and only the region 1900-800 cm$^{-1}$ is of significance in the quantitative analysis of water-based muds. FIG. 3 shows the infrared spectrum of the water-based mud from FIG. 2 after subtraction of the water spectrum; the presence of the barite and bentonite mud products and the drilled solid limestone (predominantly calcite or calcium carbonate) is clearly evident. For comparison, FIG. 4 shows the raw diffuse reflectance spectrum of the dried and crushed mud solids obtained from the liquid mud whose spectrum is shown in FIG. 2 using the prior art technique. FIG. 5 shows the infrared spectrum of an oil-based mud; the presence of the continuous oil phase, the discrete water (droplet) phase and the solids barite, organophilic clay and drilled limestone are clearly indicated. The whole ATR spectral region 4000-800 cm$^{-1}$ contains data of significance for the quantification of components in oil-based muds.

Whichever technique is used in the present invention, it is necessary to prepare calibration samples of known compositions such that the variation in infrared spectrophotometric response can be equated to the nature and composition of the mud being analysed. The preparation of test muds and construction of the calibration model is similar to that described in our co-pending EPC Applications Nos 90202795.2 and 90202796.0.

QUANTITATIVE TECHNIQUES

Water-based Drilling Fluids: Static Measurements

The components used to formulate the water-based muds which comprise the calibration standards are shown in Table 1, together with the concentration range of each component. The muds contained the polymers carboxymethyl cellulose (CMC), partially hydrolysed polyacrylamide (PHPA) and xanthan gum (XC), the commercial mud solids barite and bentonite and the drilled solids limestone, dolomite, quartz (sand) and OCMA (kaolinite). The infrared spectra of static mud samples were collected using a horizontal zinc selenide crystal; immediately after preparation, a mud sample was poured onto the plate and the spectrum collected. A calibration model for the static water-based mud was constructed by regressing the static infrared spectra of the calibration standards against their accurately known compositions; one of a number of linear multivariate regression techniques can be used as identified in K. R. Beebe and B. R. Kowalski, *An Introduction to Multivariate Calibration and Analysis,* Anal. Chem., 59, 1007A-1017A (1987). The multivariate technique used in the present case is partial least squares regression.

Figure 6:
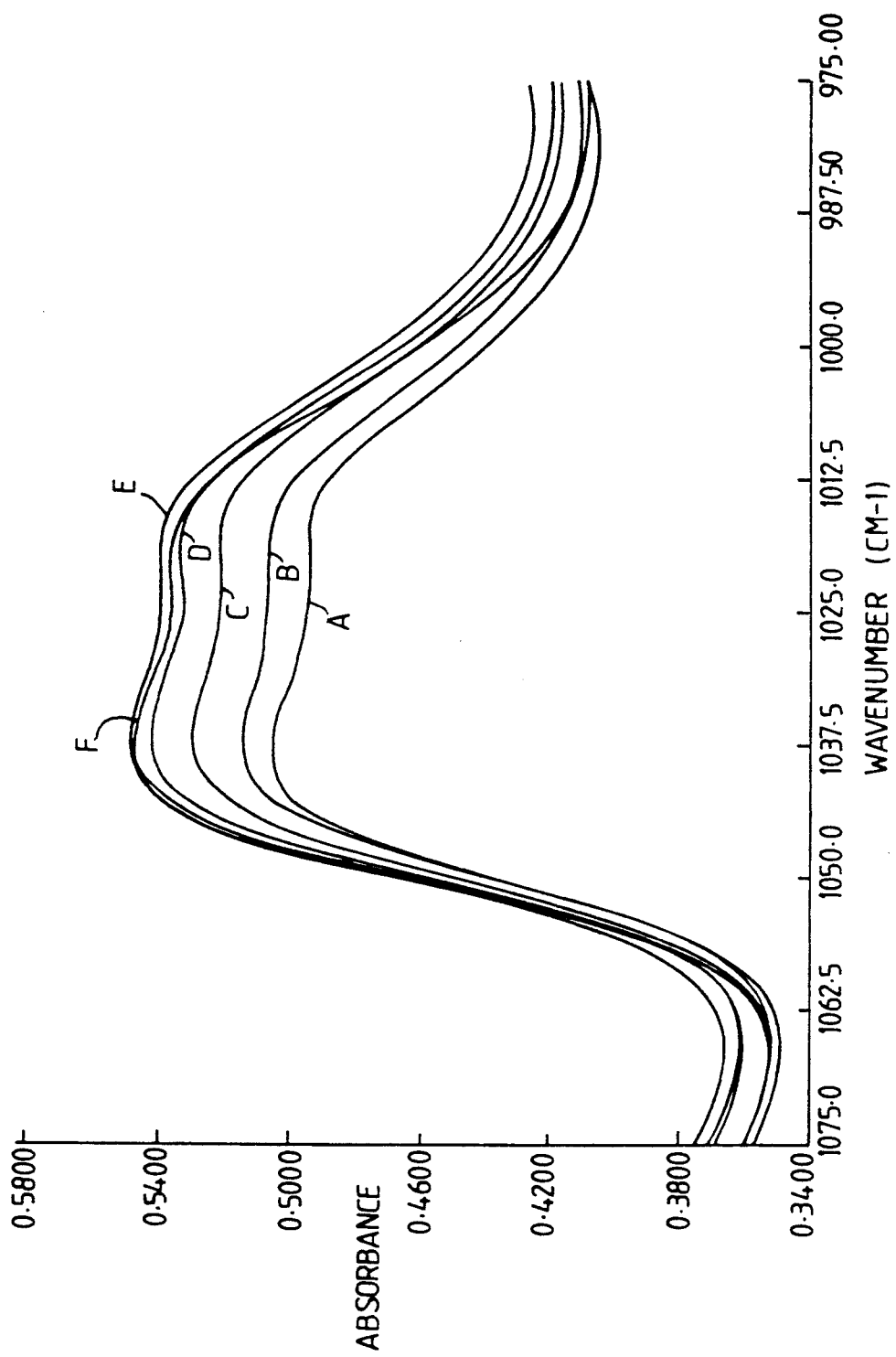
FIG. 6 Variation of absorbence of characteristic bentonite peak in bentonite-water suspension (bentonite conc.=60 g/l) with shear time. Shear time in minutes: (A) 30; (B) 120; (C) 300; (D) 450; (E) 600. Spectrum (F) shows bentonite suspension aged for 48 hours in off-line hot roller oven.
Figure 7:
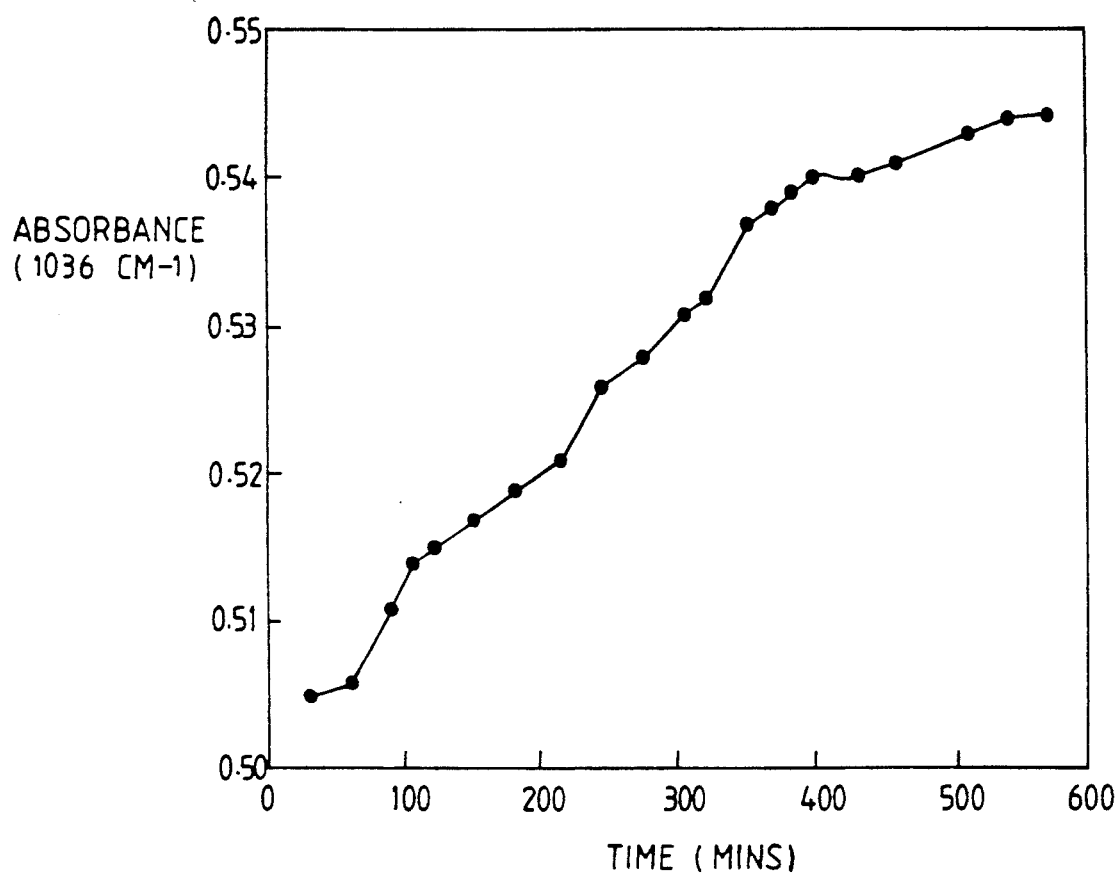
FIG. 7 Dependence of bentonite peak height ($\tilde{V}=1036$ cm$^{-1}$) on shear time of bentonite suspension (60 g/l bentonite)
Figure 8A:
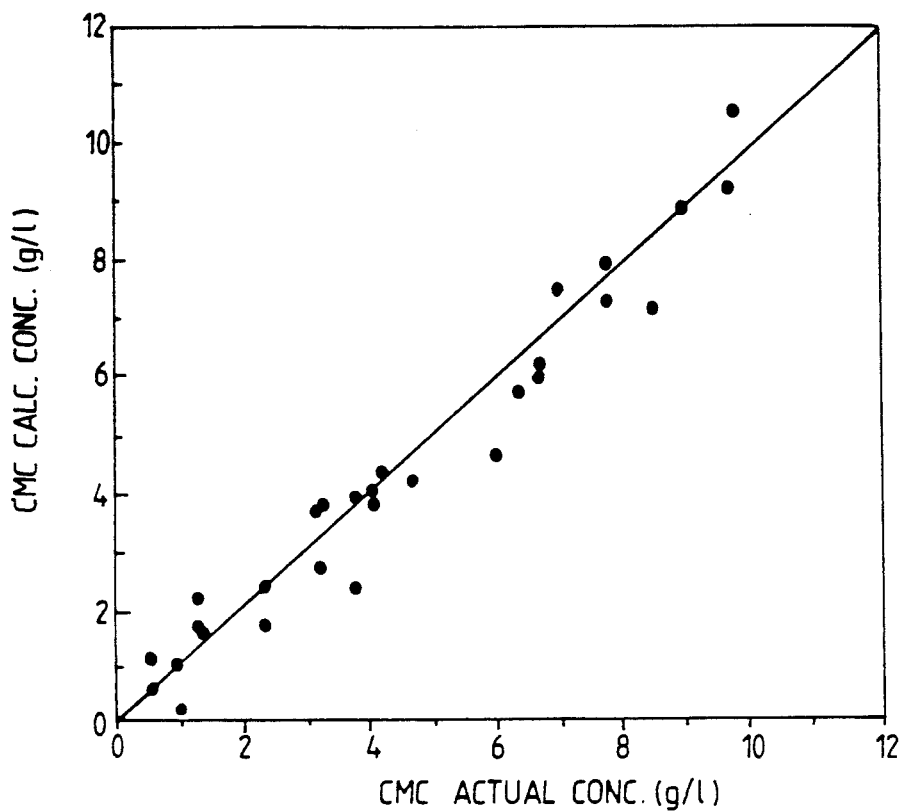
FIGS. 8A–8D Best fit of calibration model for static water-based drilling fluid to selected component compositions in calibration standards: CMC, PHPA, barite and quartz.
Figure 8B:
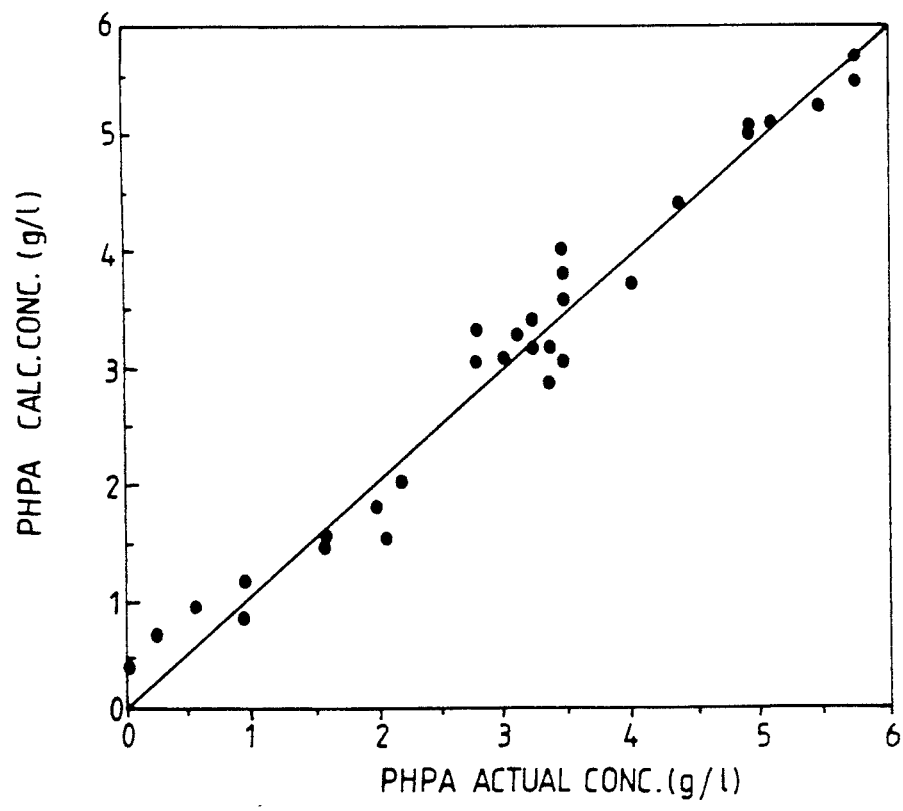
Figure 8C:
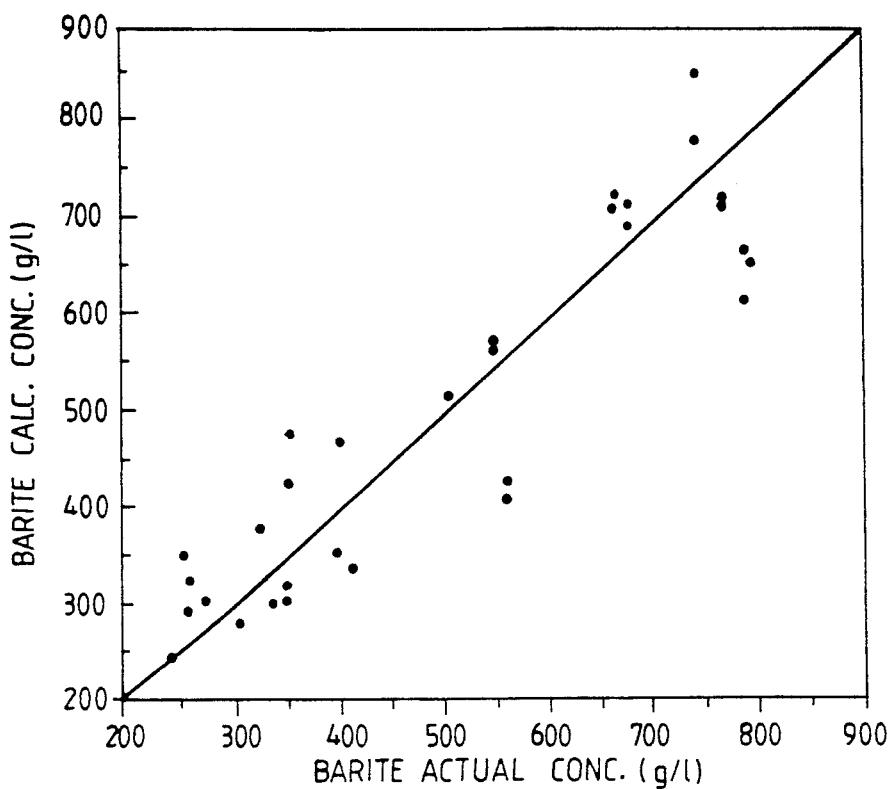
Figure 8D:
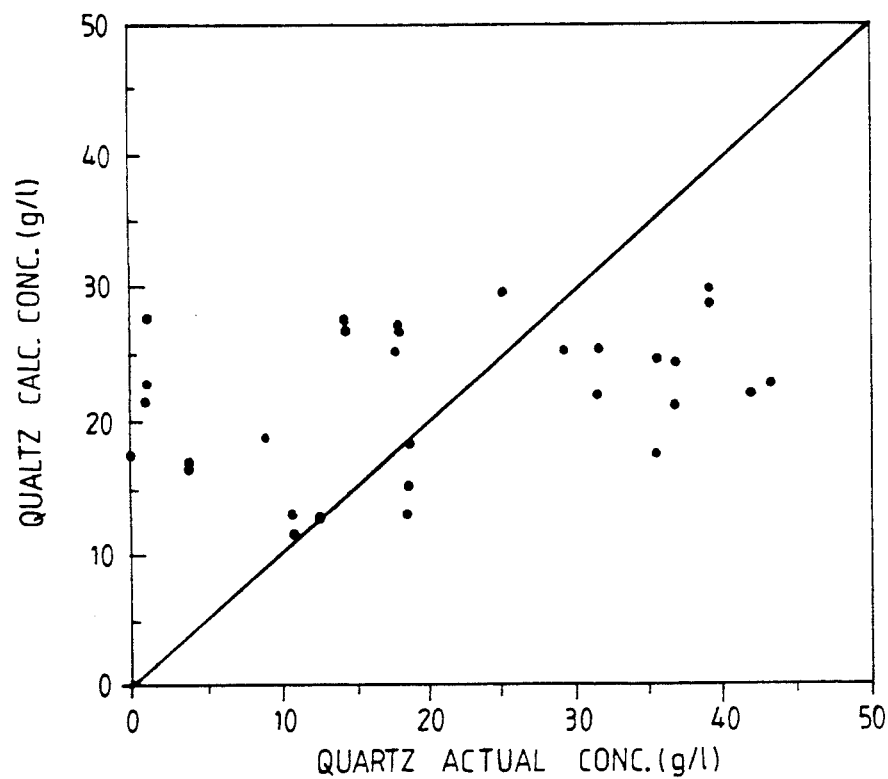
Figure 9A:
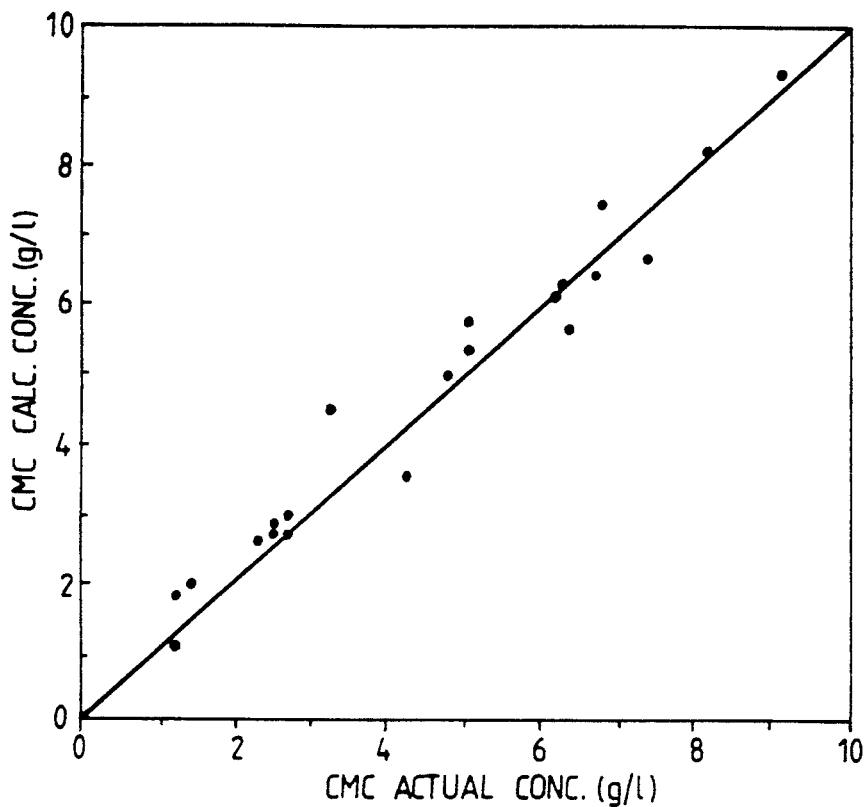
FIGS. 9A–9D Prediction of concentration of selected components in water-based mud validation samples: CMC, PHPA, barite and quartz.
Figure 9B:
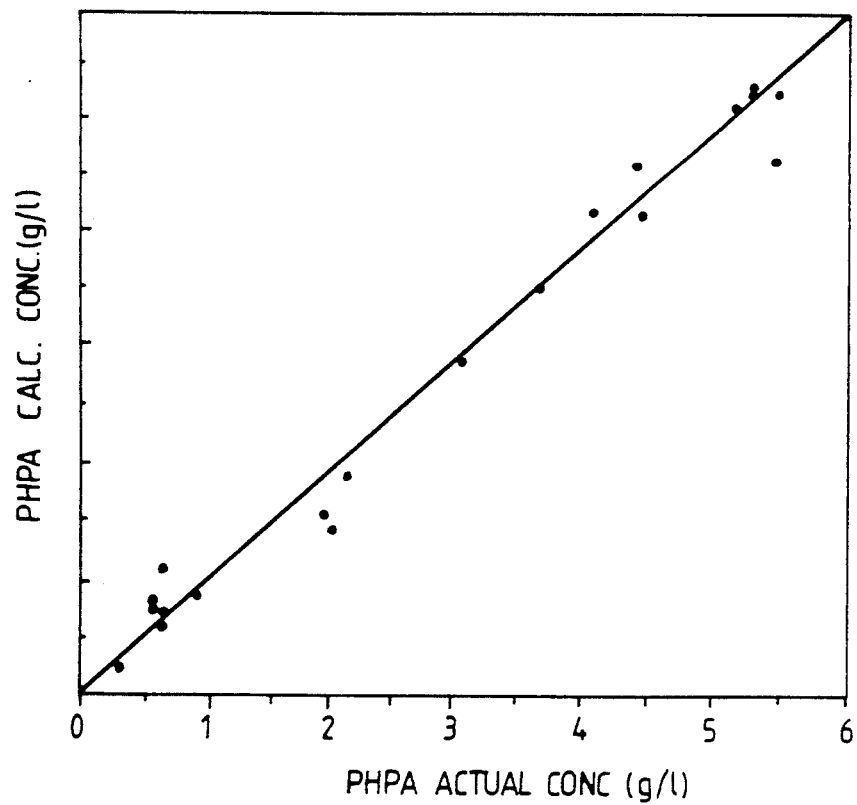
Figure 9C:
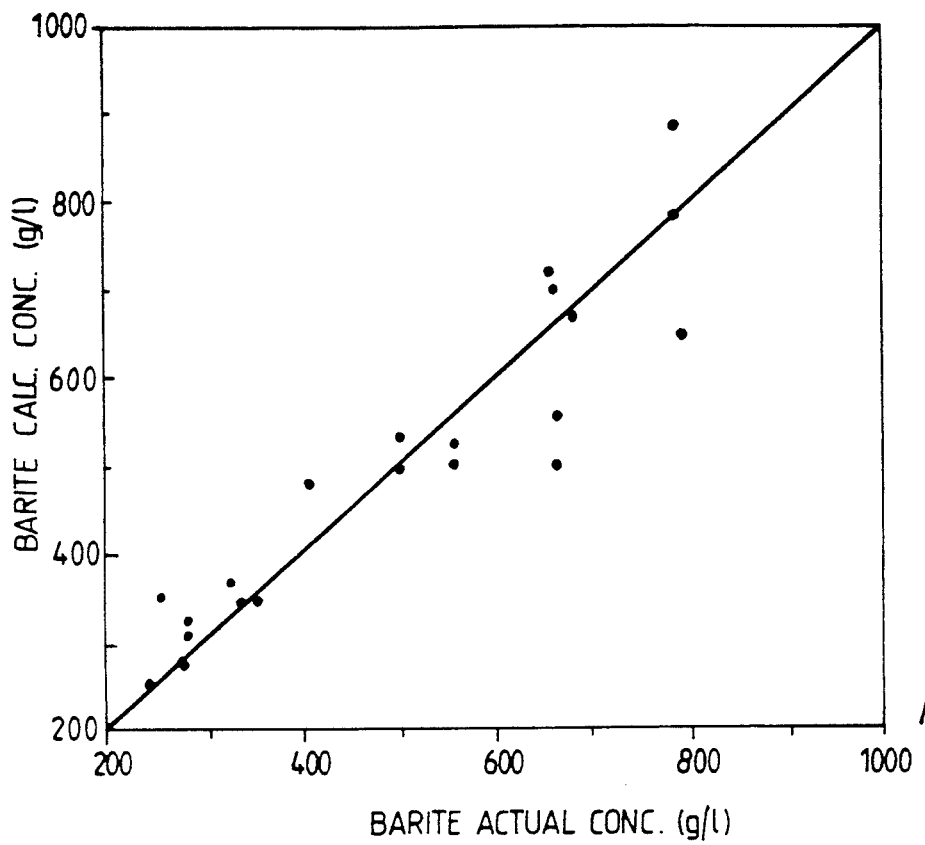
Figure 9D:
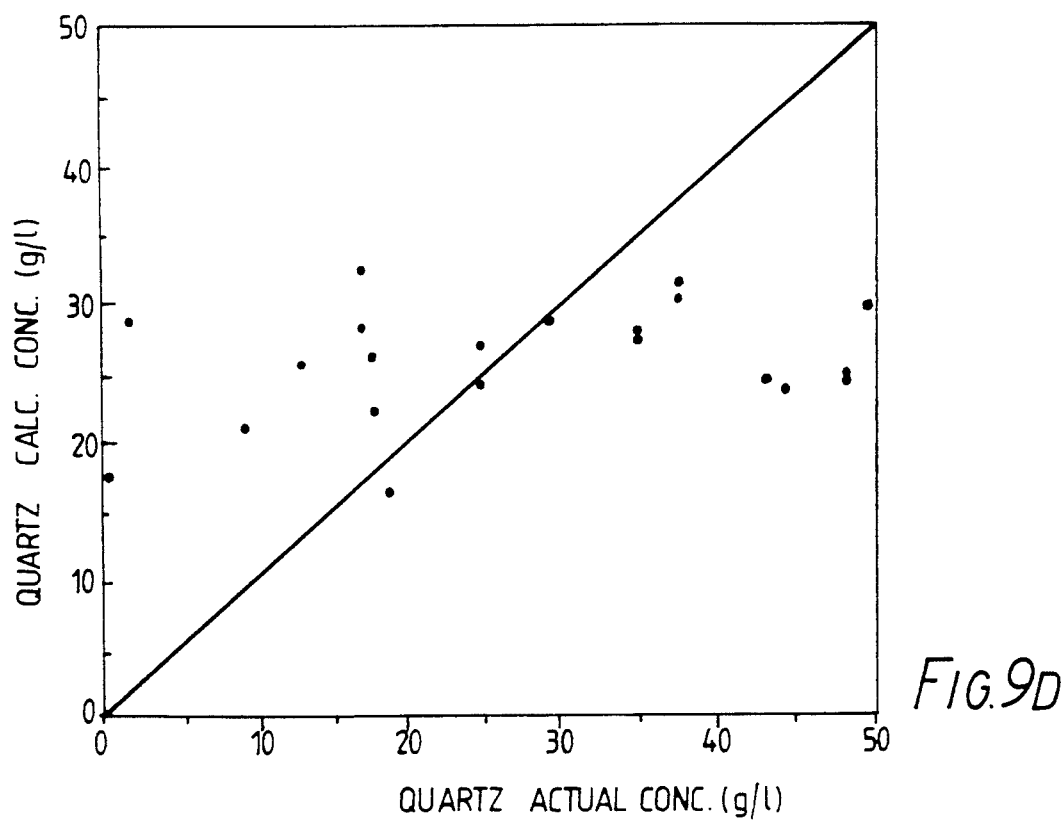

It has been found that the infrared spectrum varies according to the shear and mixing of the sample. Therefore, preparation of the drilling fluid standards used in the calibration model must also reflect the shear and mixing history of the real drilling fluids being analysed. For example, the infrared spectrum of a bentonite suspension is sensitive to its state of dispersion or hydration. FIG. 6 shows the evolution of the characteristic silicon-oxygen absorption band in the spectrum of a bentonite-water suspension as a function of the shearing time; the dependence of peak height ($\tilde{V}=1036$ cm-1) on mixing time is shown in FIG. 7. For comparison, the spectrum of a bentonite suspension hydrated for 48 hours in a conventional hot-roller oven is shown in FIG. 6(F). The preparation of the mud standards included shearing them at a fixed shear rate and for a fixed period of time. FIG. 2 shows the typical spectrum of a water-based mud. The subtraction of the spectrum of water, or the spectrum of any other such component, is not a requirement of the method nor is the assignment of infrared absorption bands to particular components since it is the whole spectrum which is monitored in multi-component systems.

Table 2 summarises the fit of the calibration model to the calibration standards and a set of validation muds. FIGS. 8A-8D show the best fit of the calibration model to the calibration standards for 4 of the components in the water-based mud; the corresponding fit to the validation samples is shown in FIGS. 9A-9D. Table 3 compares the actual and calculated concentrations for the components in two test mud samples; 10 of the 18 components quantified in the two mud samples are within 10% of their known values and 13 components are within 20%. Generally good results are obtained for the mud polymers and the solids bentonite, OCMA and dolomite, but increasingly poorer results for the solids barite, limestone and quartz. The regression model has failed to find a suitable correlation between the infrared spectra of the muds and the composition of quartz; the model has predicted the concentration of quartz in each of the standards to be approximately equal to the mean concentration in the set.

It has been found that the average particle size of the particulate matter (solid components, fines, etc) in the drilling fluid has a marked influence on the accuracy of the calibration model. Table 4 shows the mean particle diameter $d_m$ of the solid components in the calibration standards and the correlation coefficient of the fit to the calibration standards and a set of validation mud samples. The ATR technique is clearly not sensitive to the changes in the concentration of quartz and increasingly insensitive to solids whose mean particle size is larger than about 30 $\mu$m. An advantage of the ATR technique for whole liquid mud is that the presence of drilled solids of a large particle size, typically $d_m > 50$ $\mu$m, is not detected and does not interfere with the quantification of materials in solution or small particle size. If a full analysis of all of the material in the drilling fluid is required, then a wet crushing technique can be employed to reduce the particle size of the coarse material (preferably crushed to $d_m < 30$ $\mu$m).

The technique described above for the quantitative analysis of drilling fluids can be applied to the analysis of drilled cuttings separated from the mud by the shale shaker. The infrared spectra of the separated cuttings (with any retained mud products) can be collected by the ATR technique if they are crushed in the presence of a known volume of a suitable liquid to form a slurry; the mean particle size of the crushed cuttings should preferably be less than 30 $\mu$m. Water is a suitable liquid to form the slurry with cuttings from both water-based and oil-based mud. The oil retained on the drilled cuttings can be made to form an emulsion with the added water and quantified by an appropriate calibration model.

However, if the particulate matter has a significant part of the particle size distribution below this limit it may still be possible to quantify the component by this technique.

Water-based Drilling Fluids: Flowing Measurements

Figure 10:
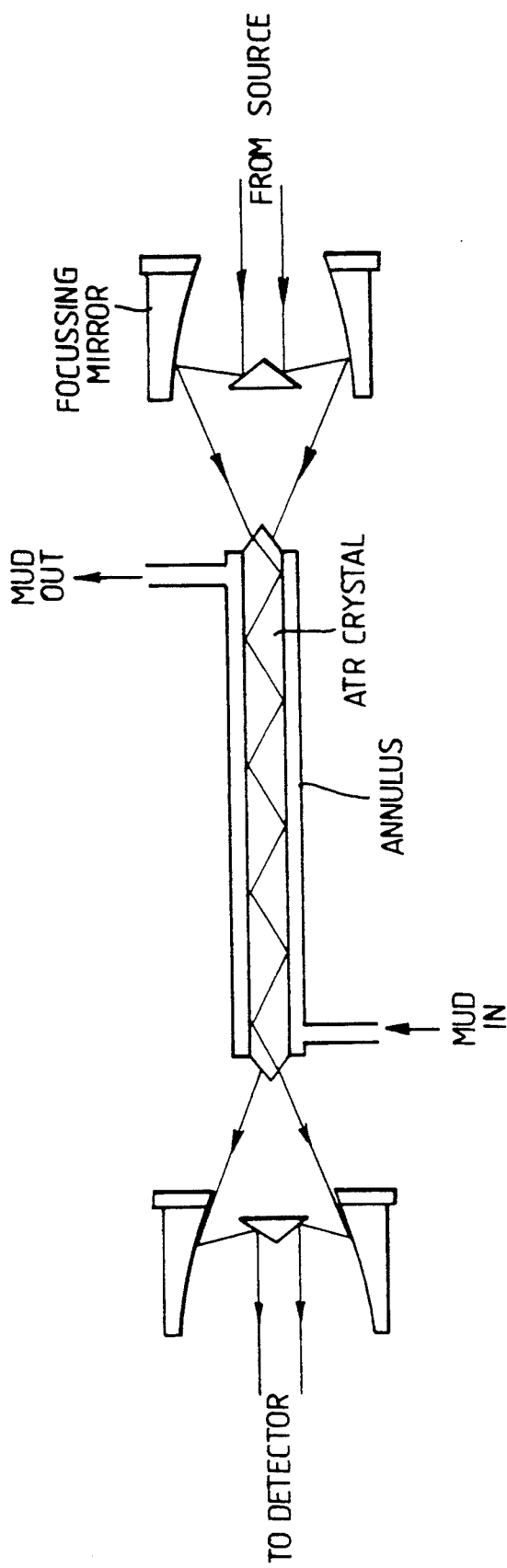
FIG. 10 Schematic of flow ATR cell for collecting the infrared spectrum of flowing mud, FIG. 11 Infrared spectrum of flowing water-based drilling fluid (static spectrum shown in FIG. 2)
Figure 11:
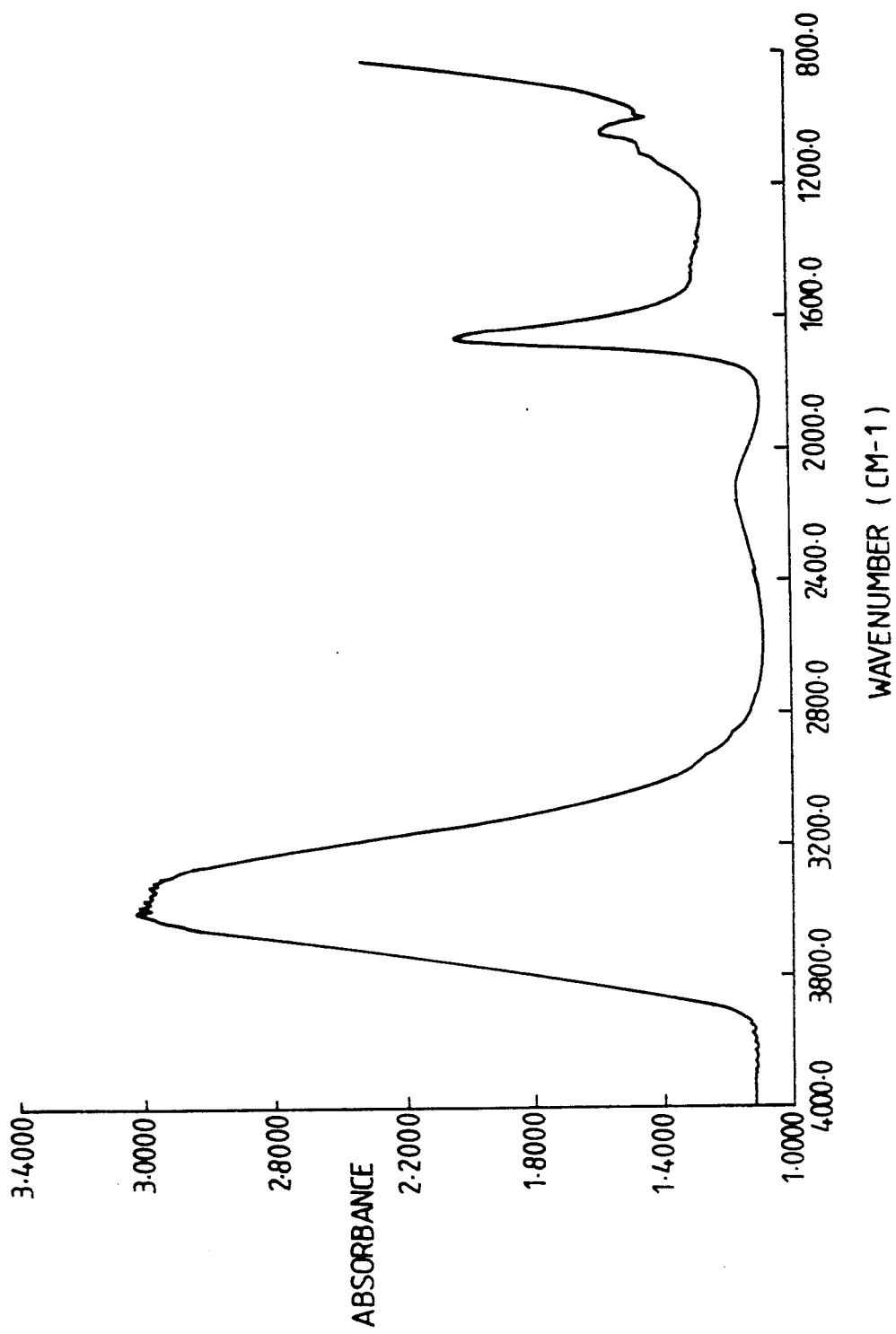
Figure 12A:
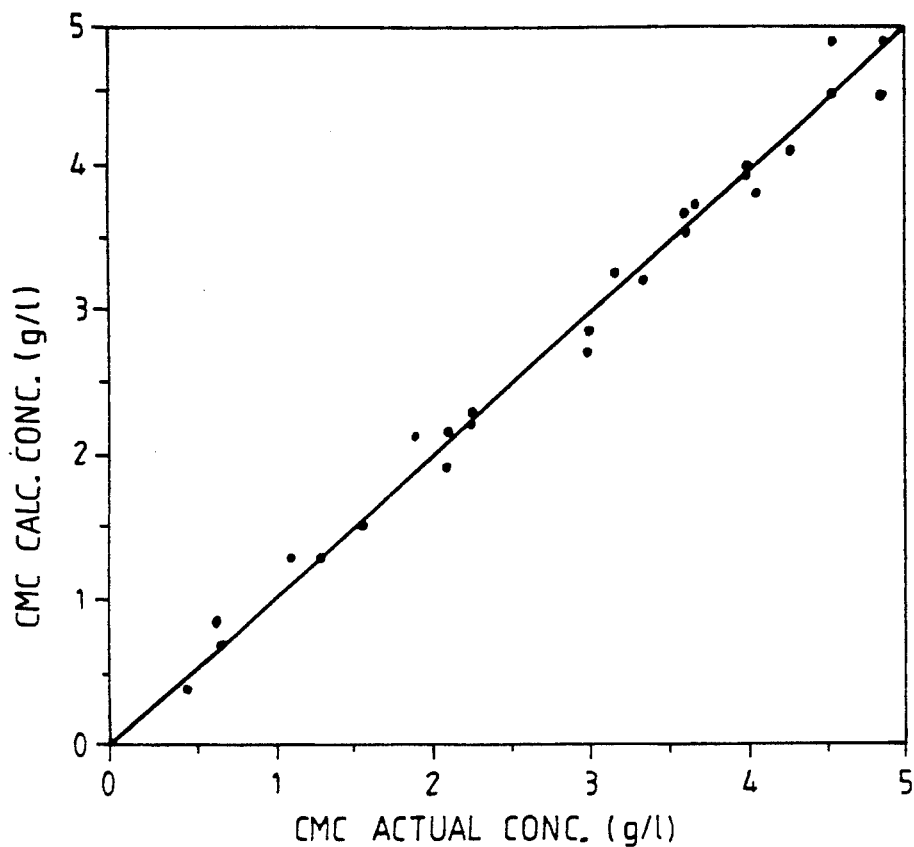
FIGS. 12A–12D Best fit of calibration model for flowing water-based drilling fluid to selected component compositions in calibration standards: CMC, PHPA, quartz nd barite.
Figure 12B:
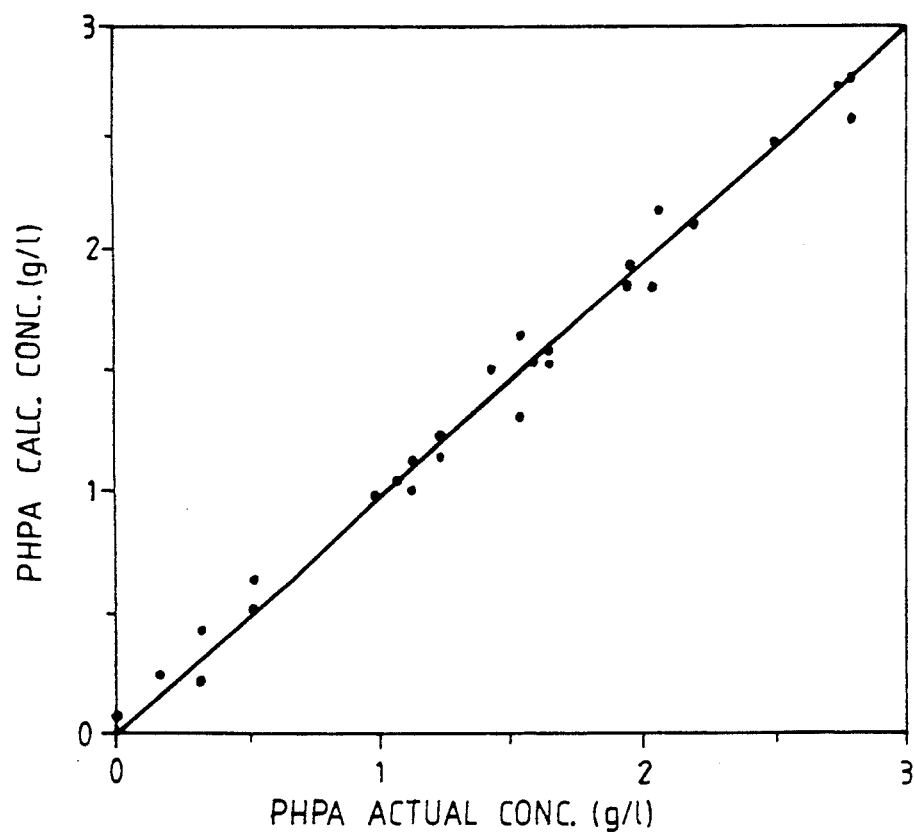
Figure 12C:
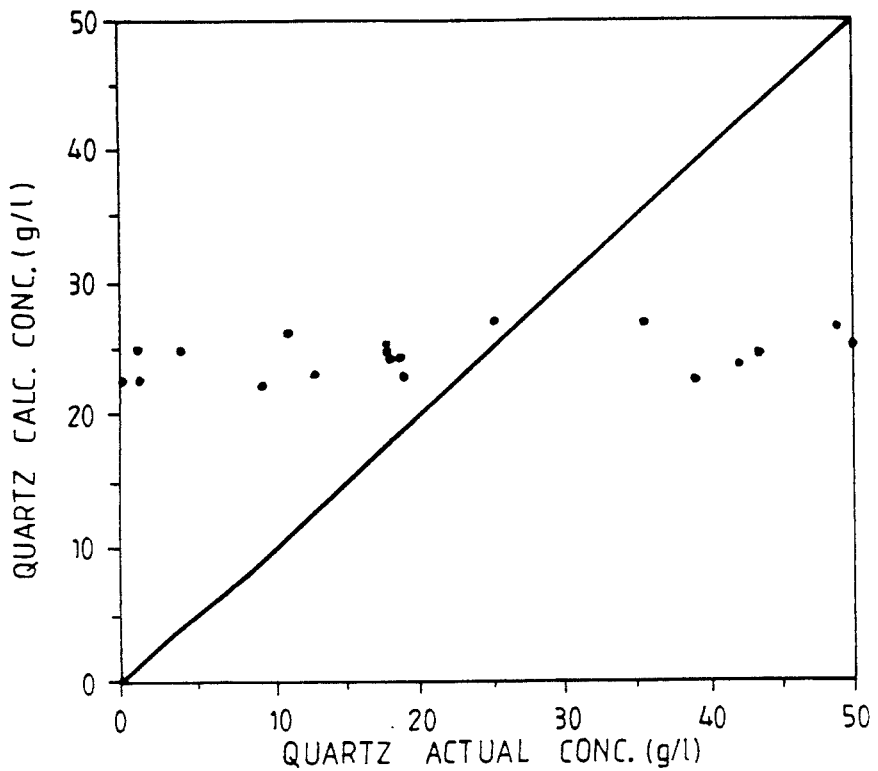
Figure 12D:
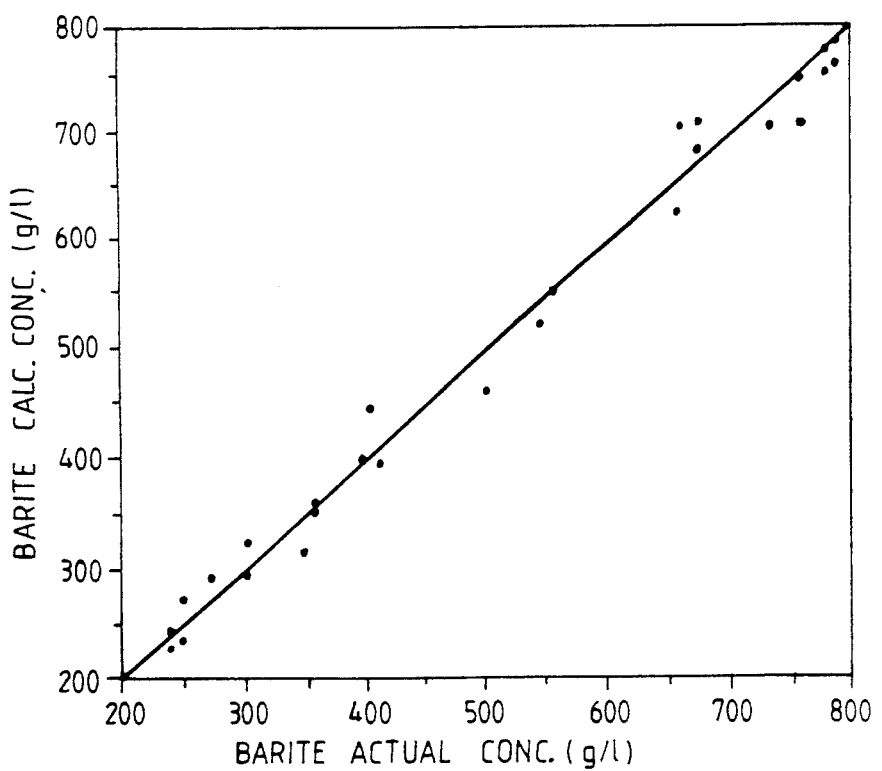
Figure 13A:
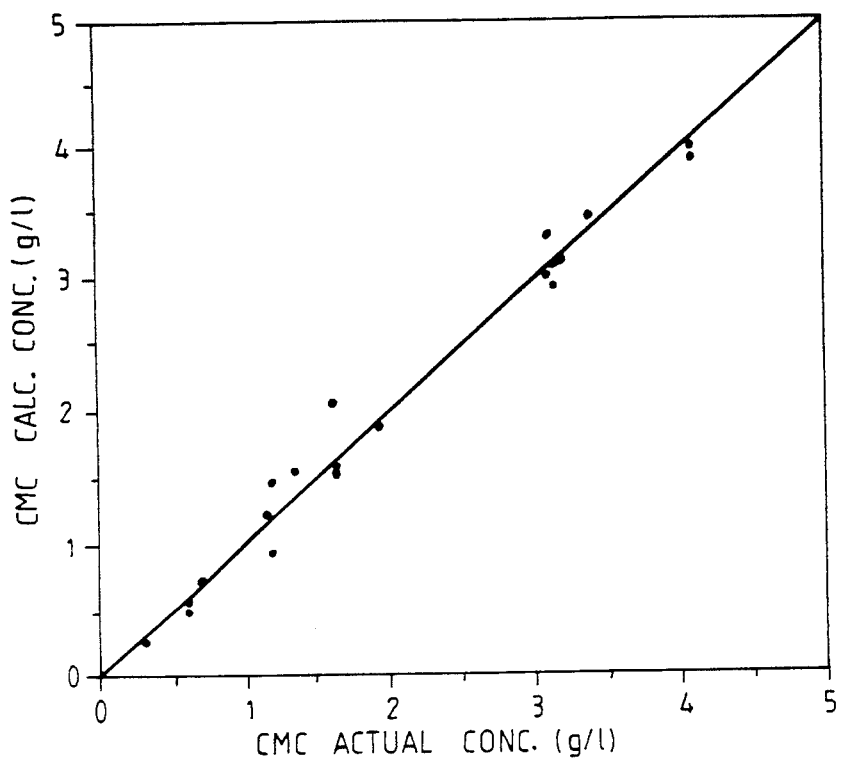
FIGS. 13A–13D Prediction of concentration of selected components in flowing water-based mud validation samples: CMC, PHPA, barite and quartz.
Figure 13B:
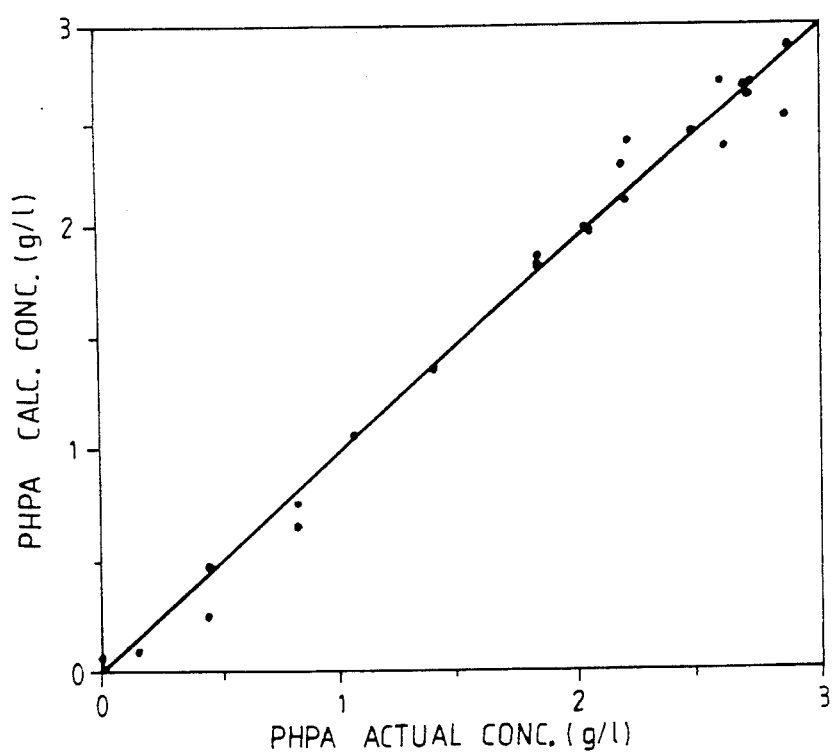
Figure 13C:
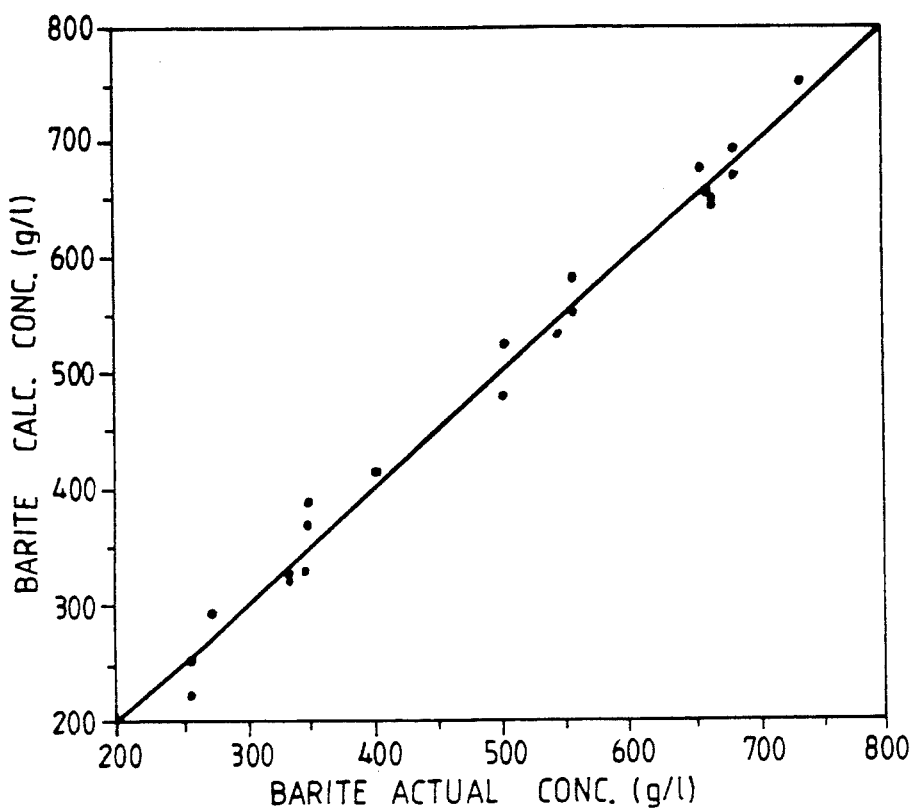
Figure 13D:
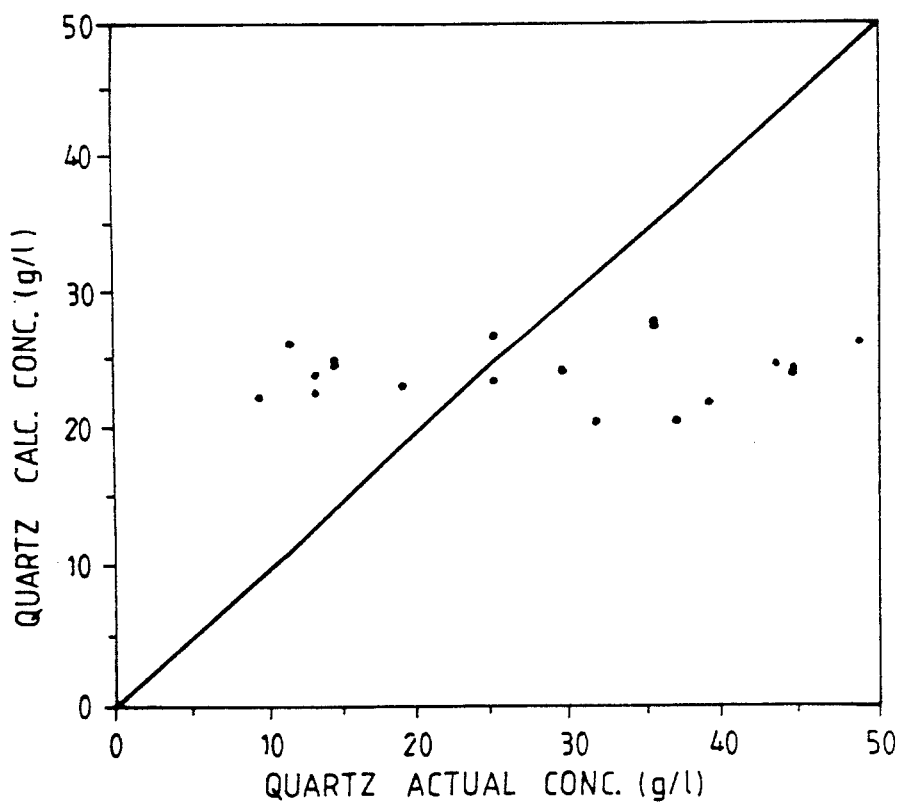
Figure 14A:
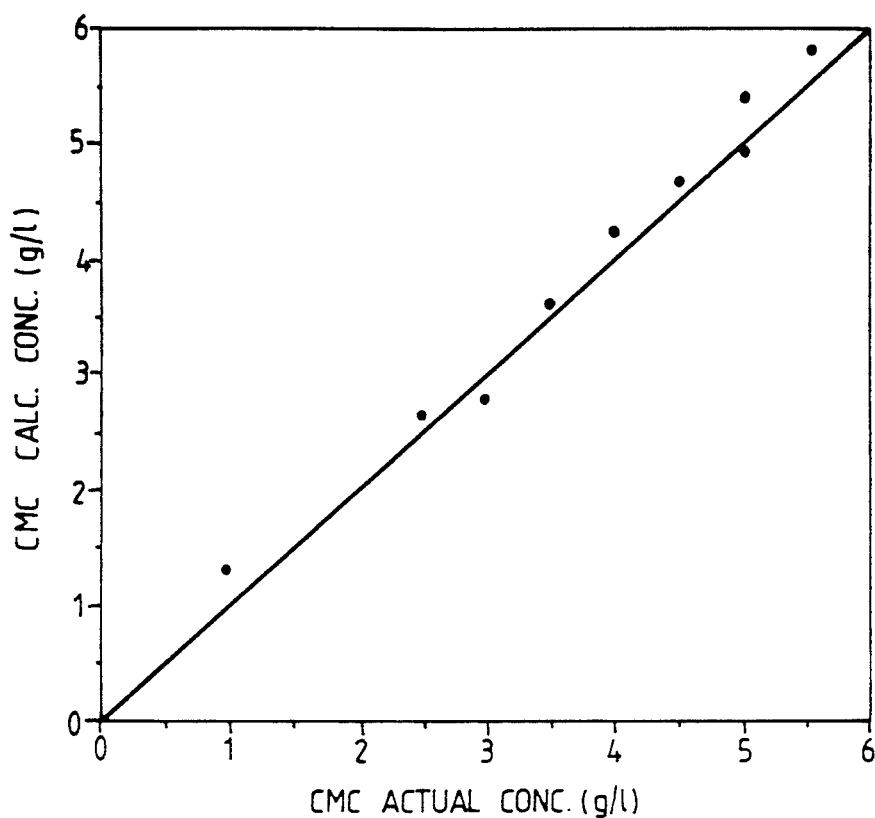
FIGS. 14A–14D Prediction of concentration of polymers CMC, XC, PHPA and guar gum in a series of validation mud filtrate samples.
Figure 14B:
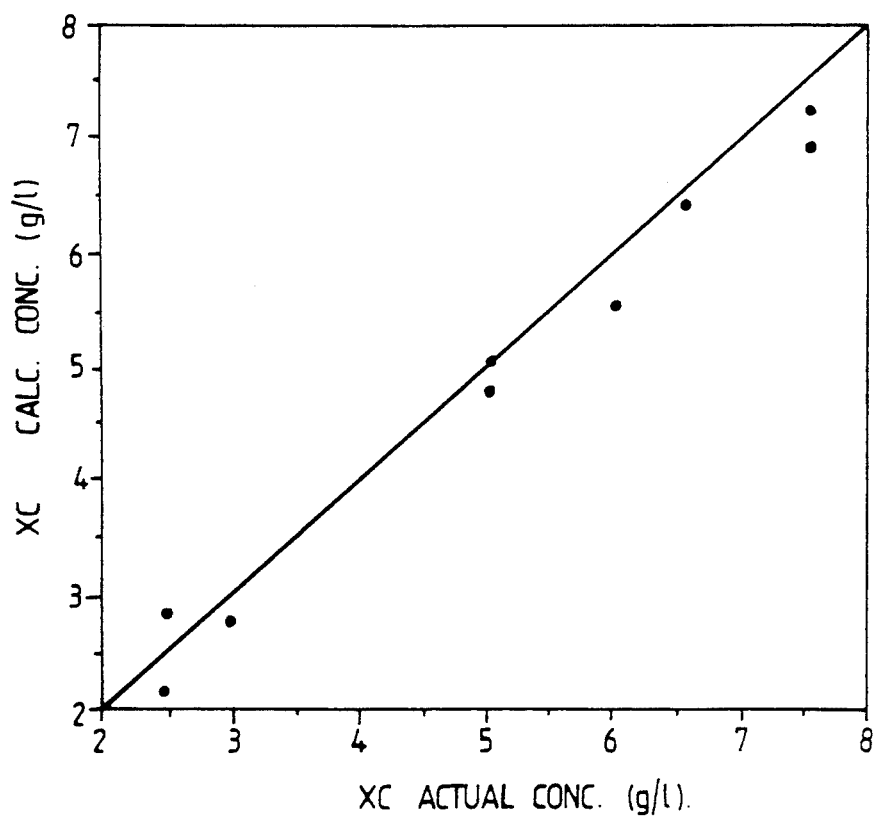
Figure 14C:
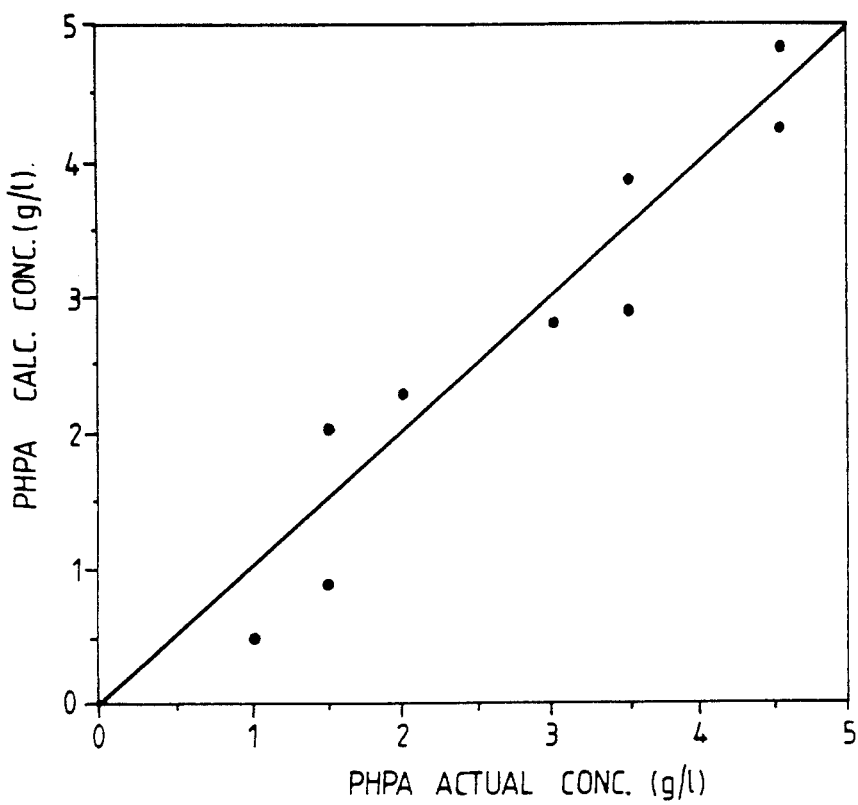
Figure 14D:
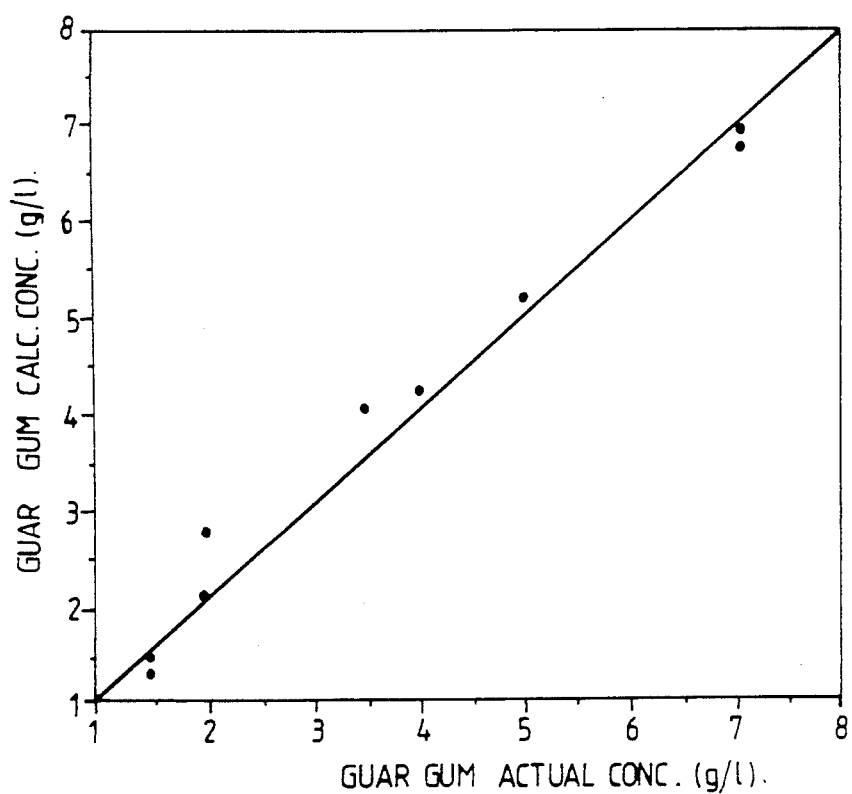
Figure 15A:
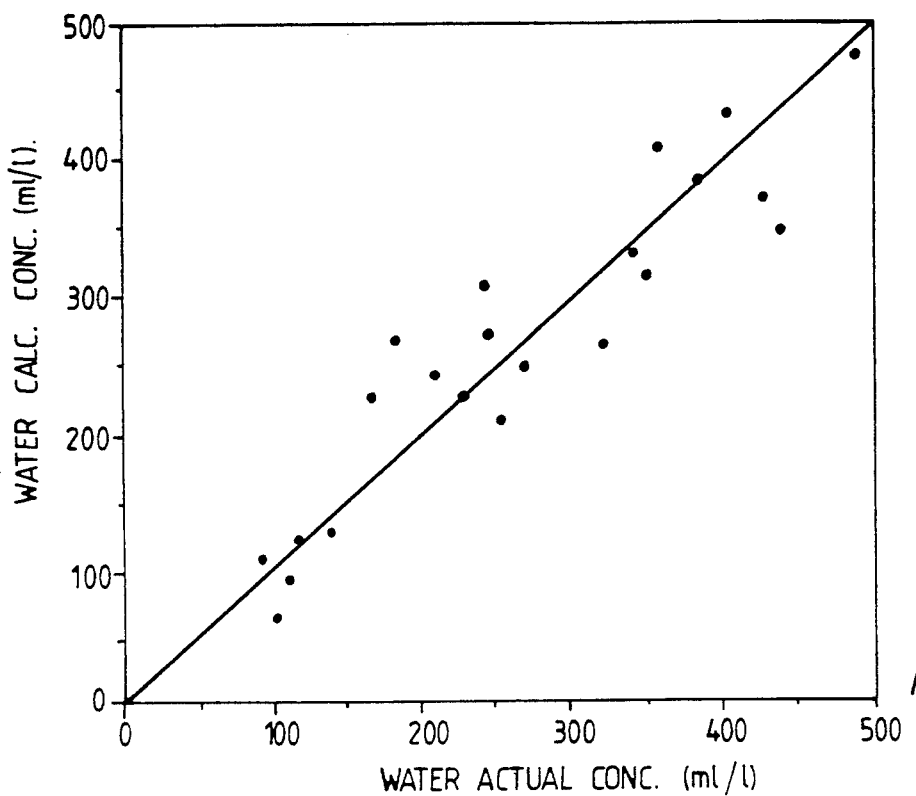
FIGS. 15A–15D Prediction of concentration of selected components in static oil-based mud calibration standards: water, base oil, water activity and limestone.
Figure 15B:
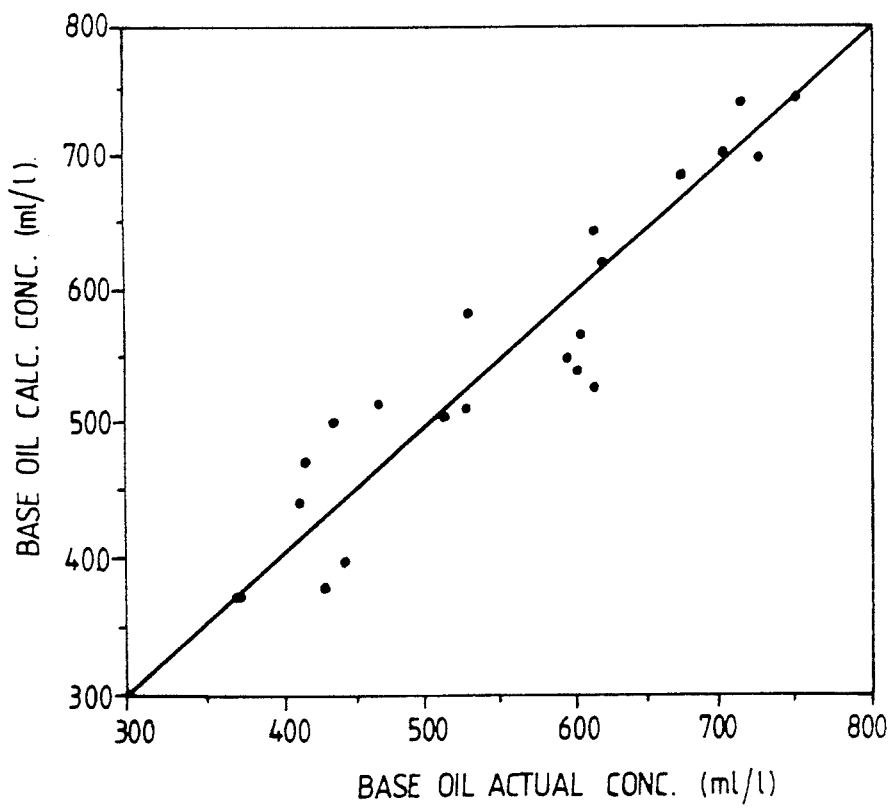
Figure 15C:
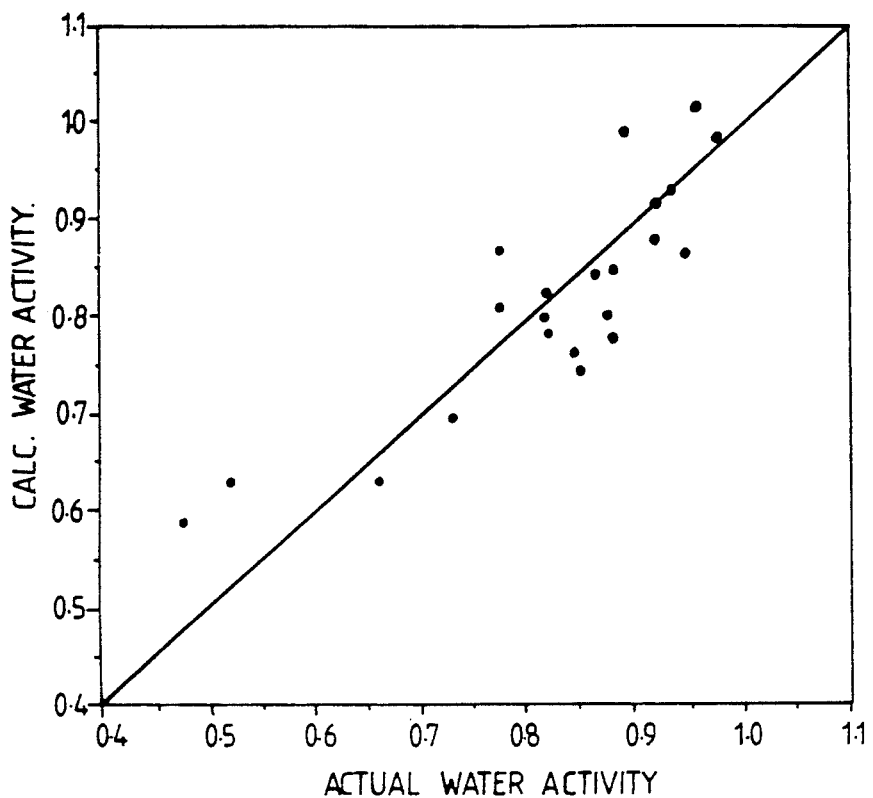
Figure 15D:
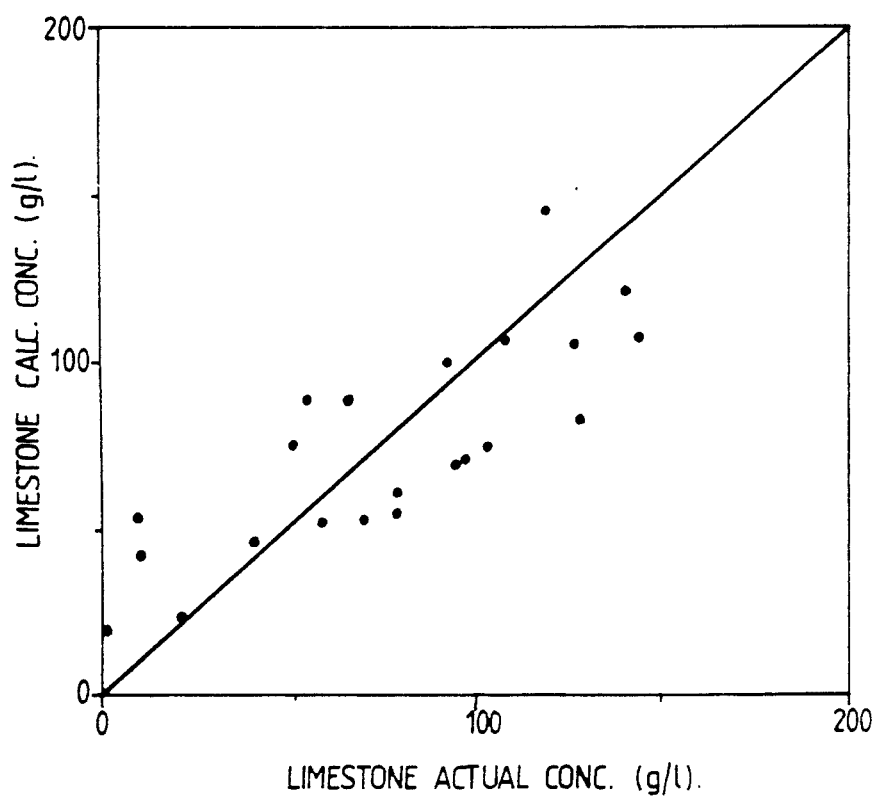
Figure 16A:
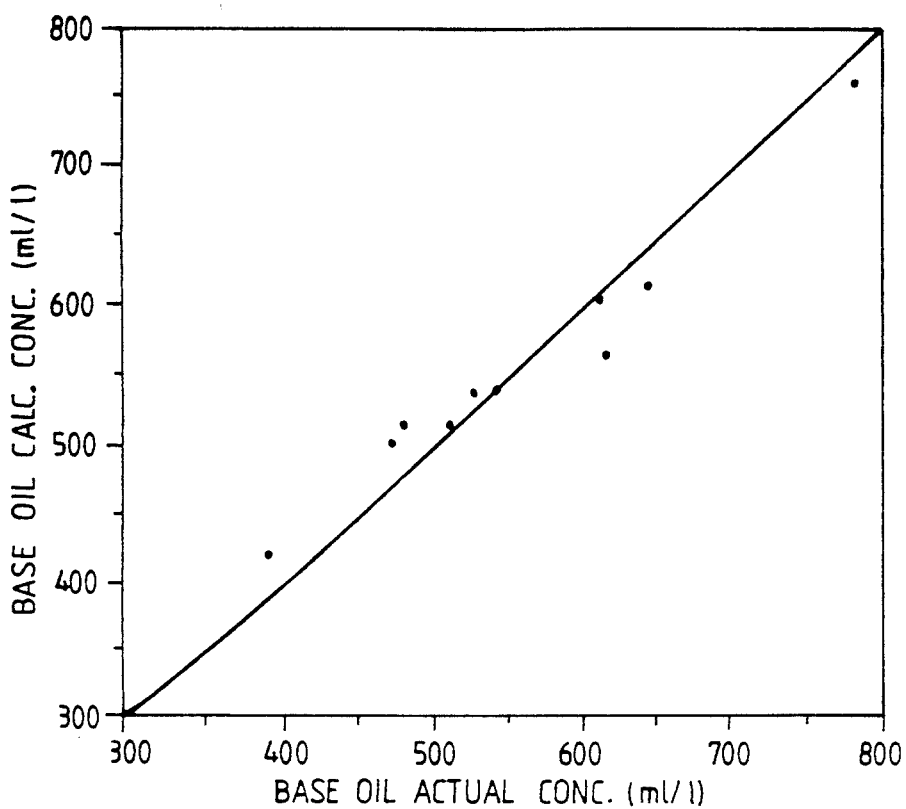
FIGS. 16A–16D Predication of concentration of selected components in static oil-based mud validation samples: base oil, water, water activity and limestone.
Figure 16B:
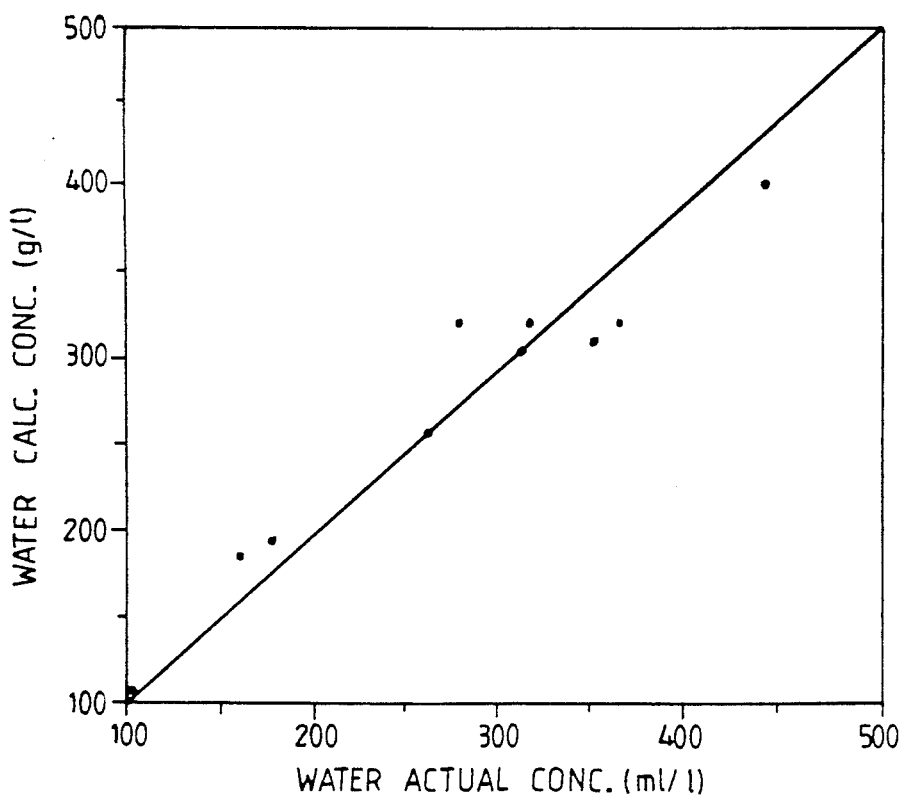
Figure 16C:
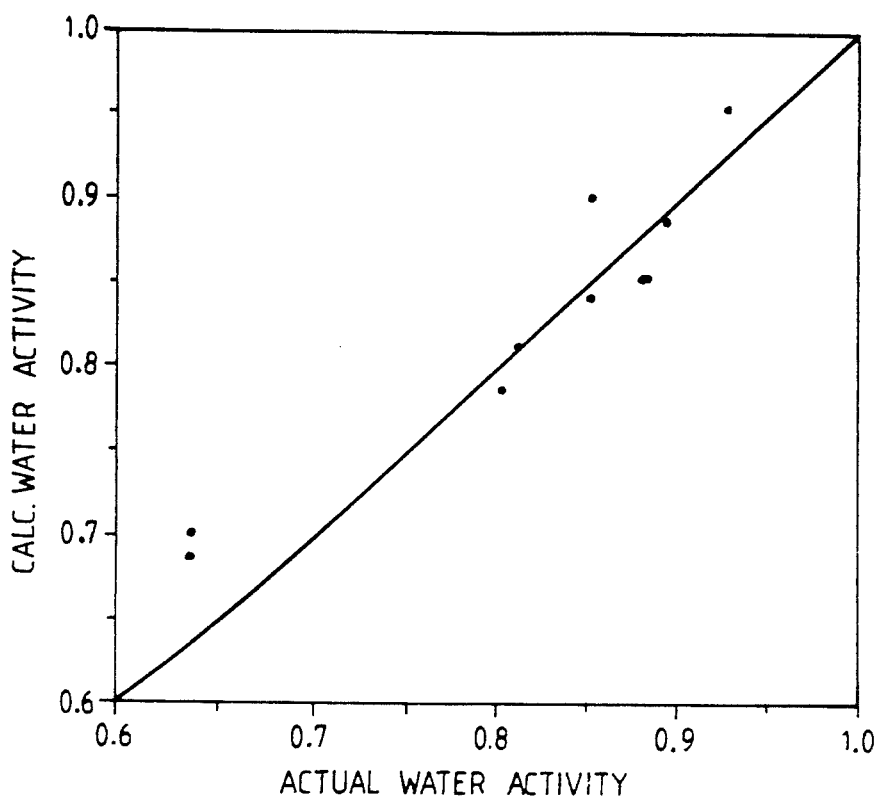
Figure 16D:
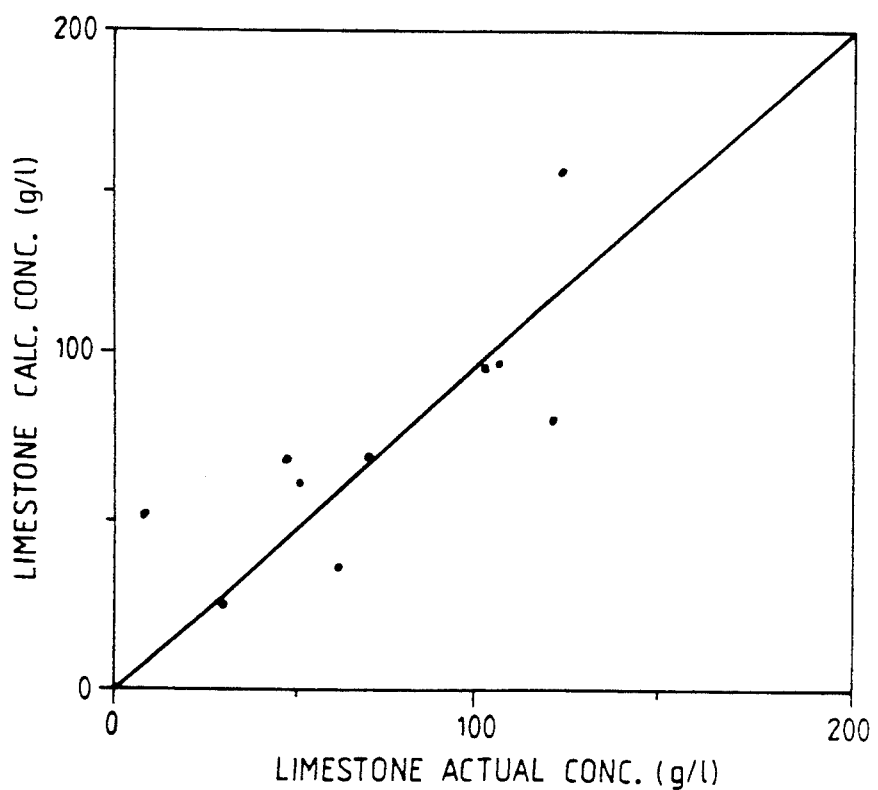

Under certain circumstances it may be more convenient to collect the infrared spectrum of flowing mud, thus enabling the concentration of components in the drilling fluids to be analysed by an on-line technique. FIG. 10 shows a schematic representation of one possible ATR flow cell. In contrast to the static ATR technique, where the ATR crystal is a flat plate, the crystal in the flow cell is cylindrical. The drilling fluid flows past the crystal by way of the annulus formed between the crystal and the wall of the flow cell. FIG. 11 shows the infrared spectrum of a flowing water-based mud sample; comparison with the static spectrum of this mud sample (FIG. 2) shows excellent agreement.

The components and concentration ranges of the standards used to construct the calibration muds are the same as for the static case and as shown in Table 1. Table 5 summarises the fit of the calibration model to the calibration standards and a set of validation muds. FIGS. 12A-12D show the fit of the calibration model to the known concentrations of 4 components in the calibration standards; the fit to the validation muds is shown in FIGS. 13A-13D. Table 6 compares the calculated and actual concentrations of mud components in two test mud samples. The calibration model developed for the flowing water-based test mud gives a prediction accuracy which is slightly better than that for the developed for the test usually used in the static model, although the accuracy of prediction of XC has declined. The flowing mud model predicts 13 of the 18 quantified components to within 10% of their accurately known values; 16 of the components are predicted within 20%.

The flowing mud model does not predict the variation of quartz in either the calibration standards or the validation samples. The infrared spectrum of flowing mud is similarly influenced by the average particle size of the solid components; if a quantitative analysis of the solids of large particle size is required (typically drilled solids), then an on-line wet crushing method will be needed.

Analysis of Polymer in Mud Filtrate

The analytical techniques provided herein for the quantification of polymers in whole mud samples overcome the problem of obtaining a representative sample of the polymer from the mud. The polymer in the filtrate obtained from a normal API filtration test is not representative of the polymer in the original mud as both the average molecular weight and the concentration of the polymer are lower in the filtrate than in the mud. However, it is conceivable that the recovery of polymer from the drilling fluid may be improved, either by chemical treatment or by a more suitable filtration technique. If a sample of mud filtrate can be obtained from the mud, then the polymer content can be estimated from its infrared spectrum using an appropriate calibration model. The filtrate can be analysed in either a static or flow ATR cell.

For the purposes of illustration a calibration model was constructed from the spectra of a series of calibration standards consisting of mixtures of the polymers CMC, XC, PHPA and guar gum dissolved in a solution of 1 molar sodium chloride. The concentration of each polymer was varied over the concentration range 1–7.5 g/l; the infrared spectra of the filtrates were collected using a static ATR cell. Table 7 summarises the fit of the calibration model to the known polymer concentrations in the calibration standards and a set of validation filtrates. FIGS. 14A–14D show the fit of the model to the concentration of each of the polymers in the validation samples and Table 8 shows a comparison between the actual and calculated polymer concentrations in two test mud filtrates. Six of the 8 predicted polymer concentrations in the two test filtrates 8 are within 10% of their accurately known values and all 8 are within 20%.

Oil-based Drilling Fluids: Static Measurements

Normal oil-based drilling fluids consist of an emulsion of water droplets in a continuous oil phase; the droplets are stabilised (i.e., prevented from coalescing to form a second continuous phase) by the presence of primary and secondary emulsifiers. Further stability is imparted to the emulsion by the addition of an organophilic clay (bentonite clay treated to give a hydrophobic surface enabling it to disperse in the oil phase); the organophilic clay also controls the fluid loss of the oil-based mud. The activity of the water (i.e., its chemical potential) in the aqueous phase in controlled by the addition of salts such as calcium chloride. Ideally the activity of the water in the oil-based mud is made equal to the activity of the water in the formations (particularly shales); such oil-based muds are commonly termed balanced activity muds. Several techniques have been advocated to determine the water activity of oil-based muds, including measurement of the salt concentration in the aqueous phase and direct determination of the vapour pressure of the water by a suitable hygrometer. Barite is added to the mud to control its density.

Table 9 shows the concentration range of the components used to formulate the calibration standards. The calcium chloride concentration in the aqueous phase of the calibration standards is varied to enable the water activity of the mud to be determined from the infrared spectrum; the water activity of each mud standard can therefore be considered as equivalent to a mud component. Although calcium chloride itself has no significant spectrum in the spectral region covered by ATR techniques (4000–800 cm$^{-1}$), its presence in aqueous solution has a marked effect on the infrared spectrum of water. The water activity of the calcium chloride solutions can be calculated either from the theory of electrolyte solutions or measured directly, e.g., by vapour pressure osmometry.

The infrared spectra of static oil-based mud samples were collected on a flat ATR crystal; FIG. 5 shows an example of a static oil-based mud spectrum. The infrared spectra of oil-based muds are markedly dependent on their shear and mixing history; consequently it is necessary to ensure that the calibration muds have been prepared to reflect the shear and mixing history of the mud samples to be analysed.

Table 10 shows a summary of the fit of the calibration model to the calibration standards and a series of validation test muds. FIGS. 15A–15D and 16A–16D show the fit of a calibration model to the concentration of 4 components in the calibration and validation mud samples. The model is able to both fit the variation of water activity in the oil-based standards and predict it accurately in a series of validation muds. Limestone is poorly predicted by the calibration model due to its large average particle size. Table 11 shows a comparison between the calculated and actual concentrations of components in two test mud samples; 13 of the 18 predicted concentrations are within 20% of their accurately known values and 8 of these are within 10%. The performance of the static oil-based model is comparable to the calibration models developed for the static and flowing water-based muds.

Oil-based Drilling Fluids: Flowing Measurements

Figure 17:
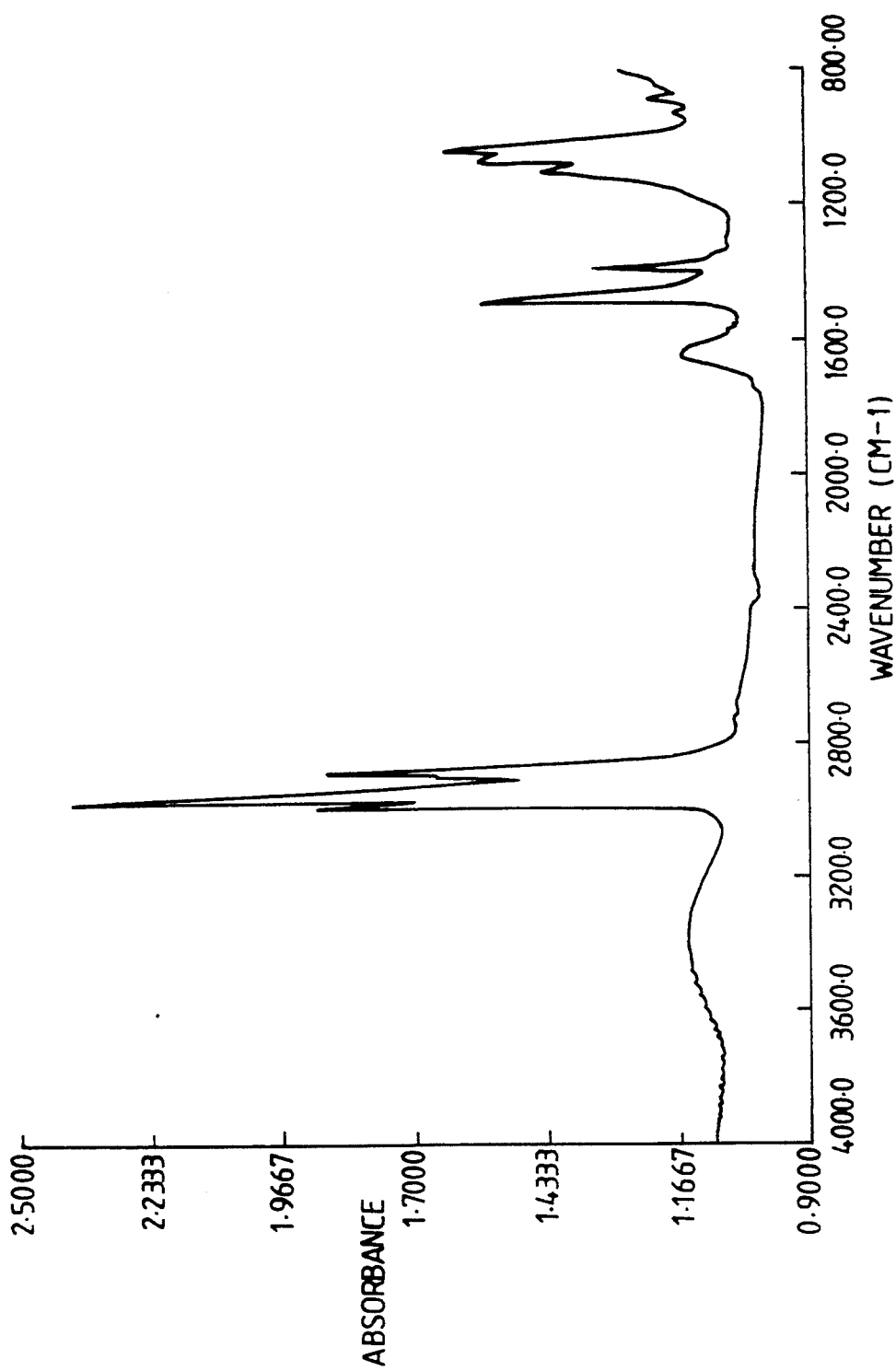
FIG. 17 Infrared spectrum of flowing oil-based mud (static mud shown in FIG. 5)
Figure 18A:
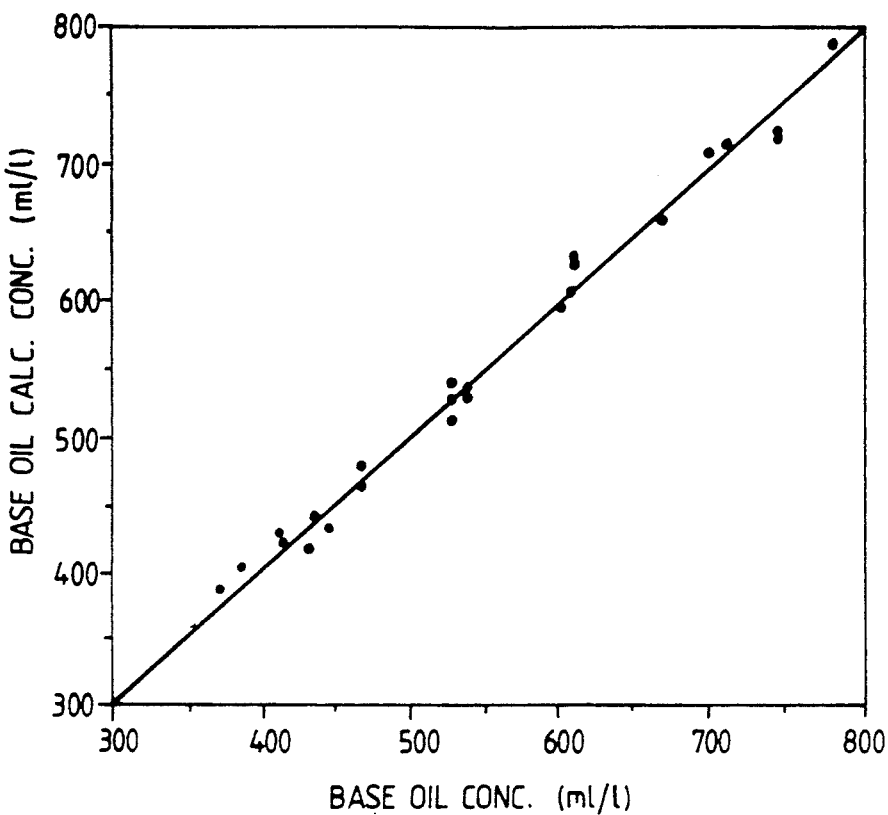
FIGS. 18A–18D Prediction of concentration of selected components in flowing oil-based mud calibration standards: base oil, water, water activity and limestone.
Figure 18B:
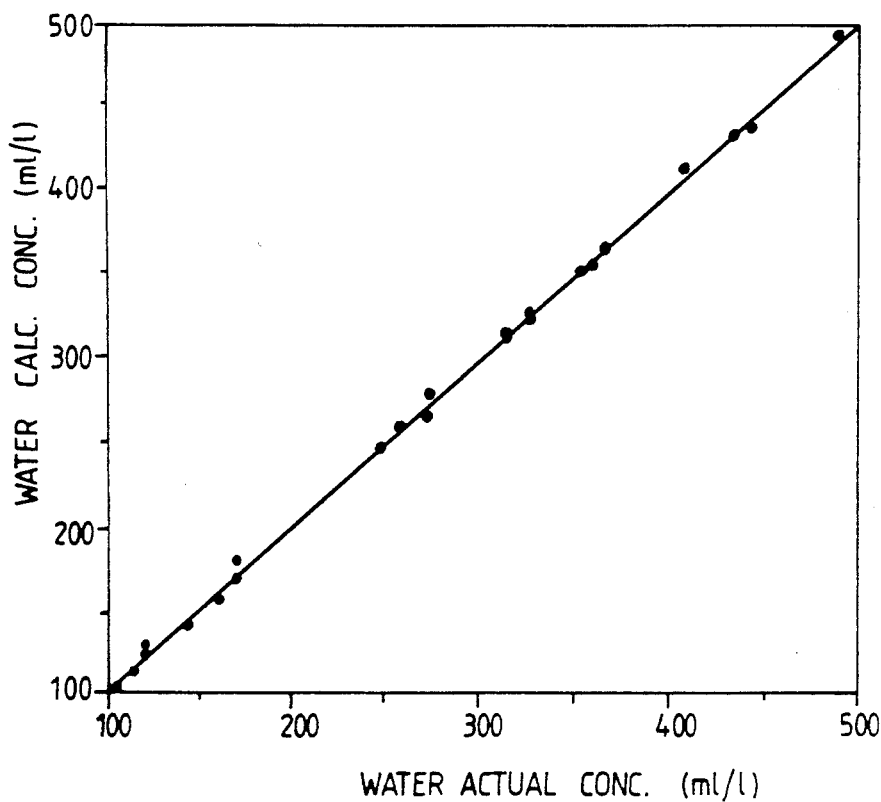
Figure 18C:
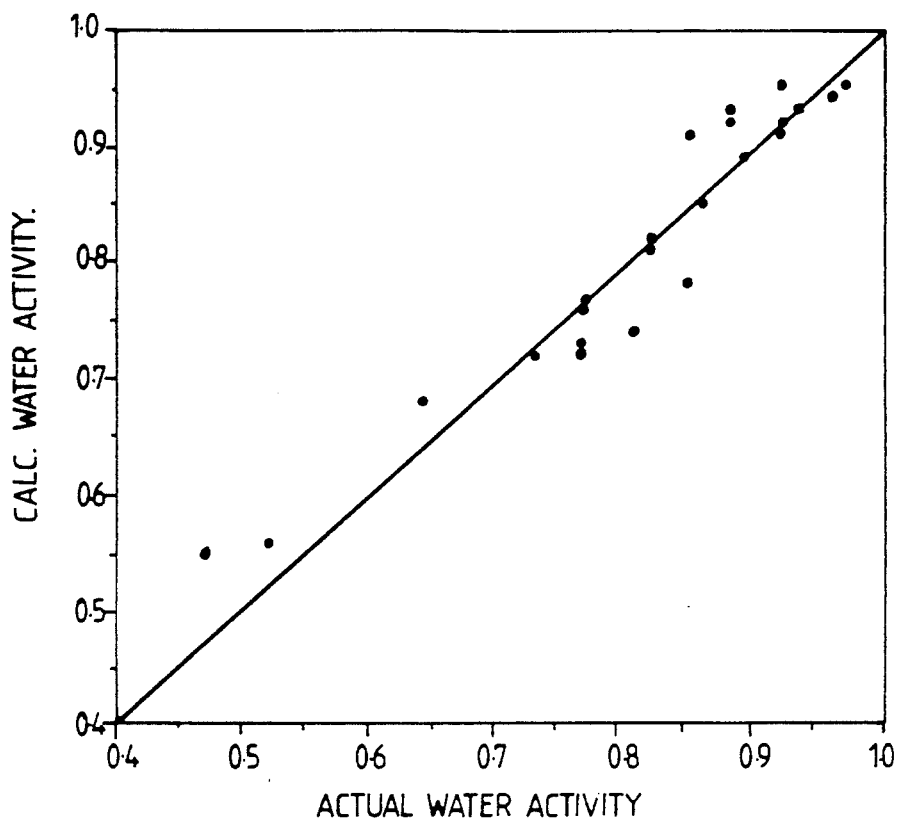
Figure 18D:
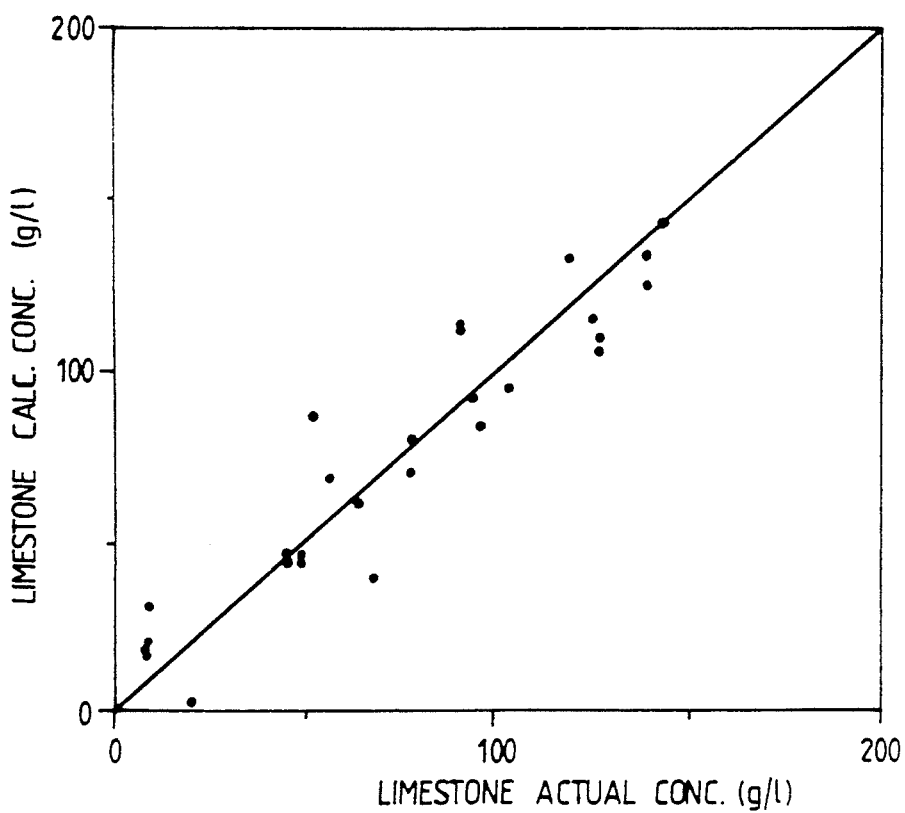
Figure 19A:
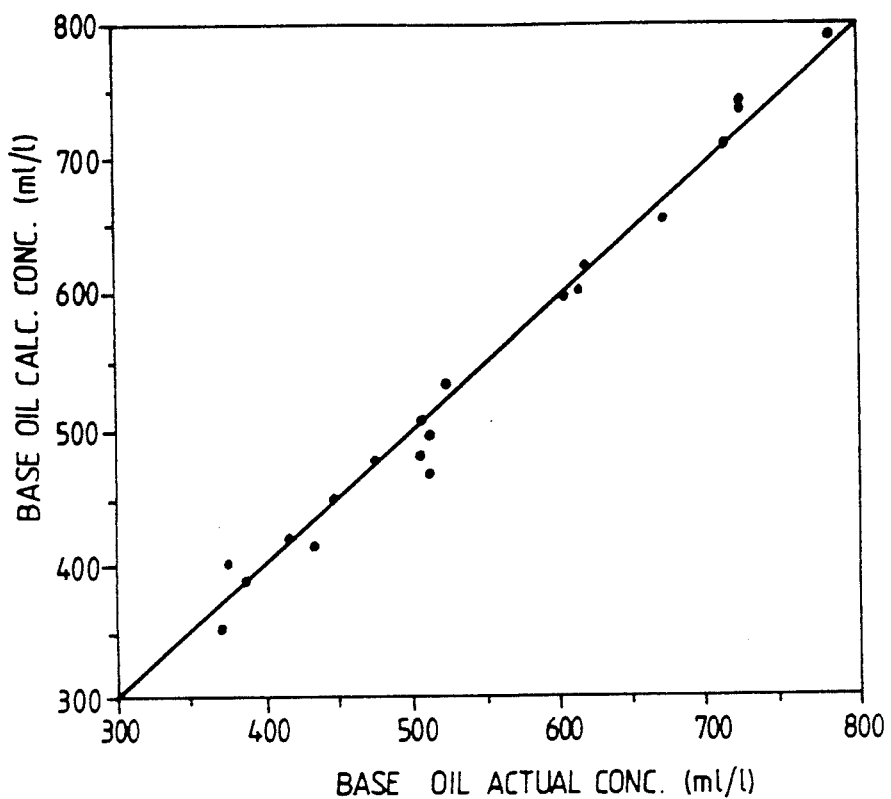
FIGS. 19A-19D Prediction of concentration of selected components in flowing oil-based mud validation samples: base oil, water, water activity and limestone.
Figure 19B:
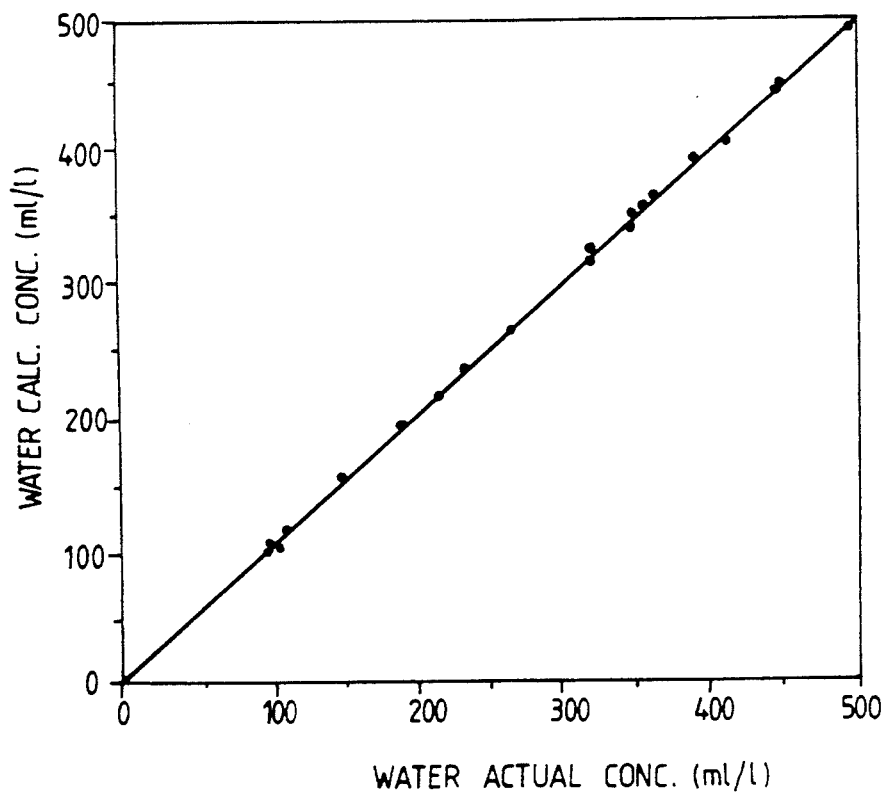
Figure 19C:
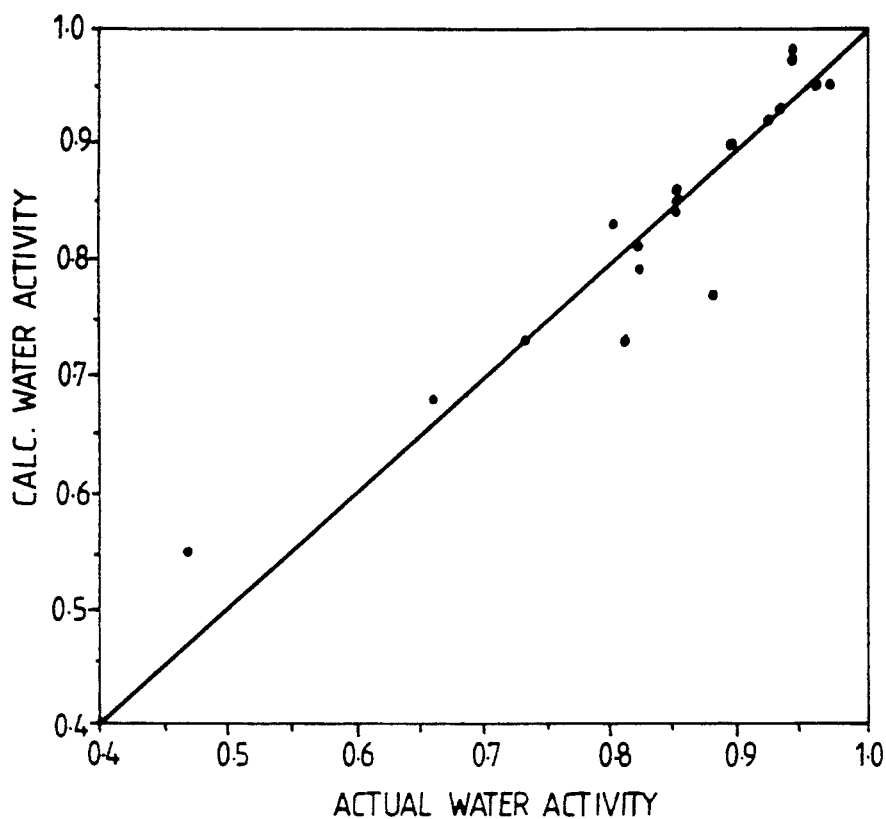
Figure 19D:
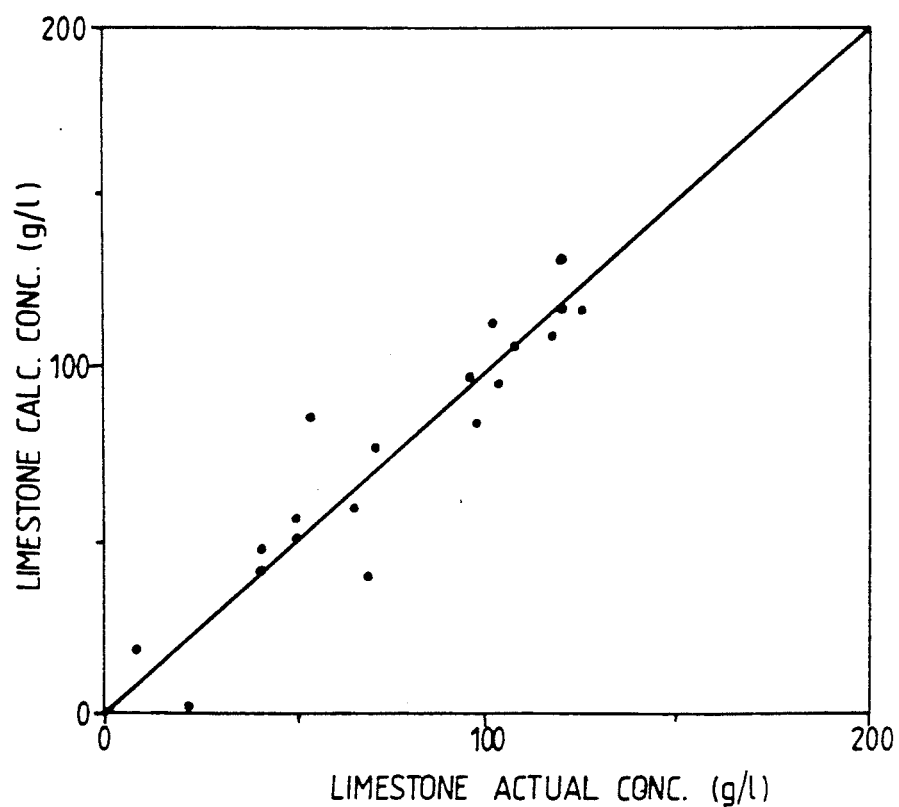

The spectra of flowing oil-based drilling fluids can be collected from the ATR flow cell shown in FIG. 10. FIG. 17 shows the infrared spectrum of a flowing oil-based mud sample; comparison with the static infrared spectrum (FIG. 5) shows excellent agreement. A calibration model was constructed using the infrared spectra of flowing mud standards whose composition range is shown in Table 5. Table 12 shows a summary of the fit of the calibration model to the calibration standards and a set of validation muds. FIGS. 18A–18D and 19A–19D show the fit of the calibration model to the concentration of 4 components in the calibration standards and the validation muds. Table 13 shows the comparison between the calculated and actual concentration of components in two flowing oil-based mud test samples; 9 of the 18 predicted concentration are within 10% and 12 within 20% of their accurately known values. The flowing oil-based mud techniques give results comparable to the static oil-based mud technique.

Mud Properties and Spectral Data

It may be advantageous to include other mud measurements, particularly physical measurements such as density, API fluid loss, plastic viscosity and yield point, in the calibration (regression) models which have only contained spectral and concentration measurements in previously proposed techniques. One approach is to use data from non-spectral mud measurements to enhance the prediction of component concentration. The calibration model is constructed from the regression of the infrared spectra and the mud measurements against their accurately known compositions, i.e., the mud measurements are equivalent to spectral measurements. The prediction of concentration in an analyte mud sample is achieved by using both the infrared spectrum and the measured property of the sample. Another approach is to predict the mud measurement or property from the measured infrared spectrum, i.e., the mud measurement or property is considered equivalent to a component concentration. The calibration model consists of a regression of the infrared spectra of a set of standards against their accurately known compositions and mud measurements. This approach may be particularly useful for on-line continuous measurements where sampling for batch measurements may be inconvenient or difficult. A combination of the two approaches can be used, i.e., the use of one mud measurement/property with spectral data to predict component concentrations and a different mud measurement/property.

Figure 22A:
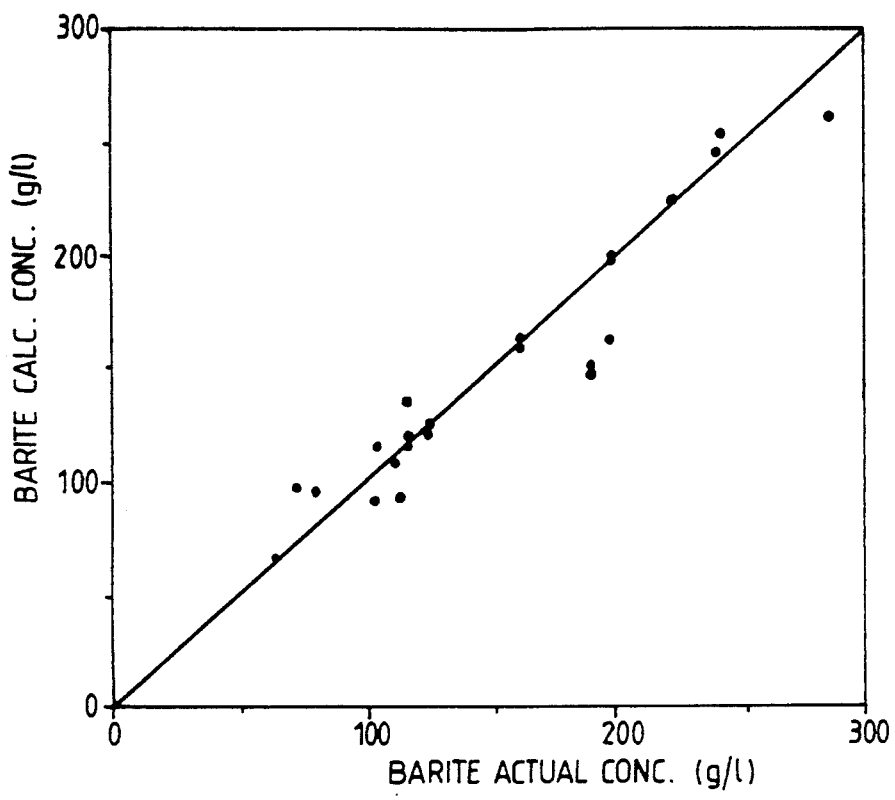
FIGS. 22A-B Prediction of barite concentration in flowing oil-based mud: (A) calibration model using spectral and mud density data, (B) calibration model using spectral data only.
Figure 22B:
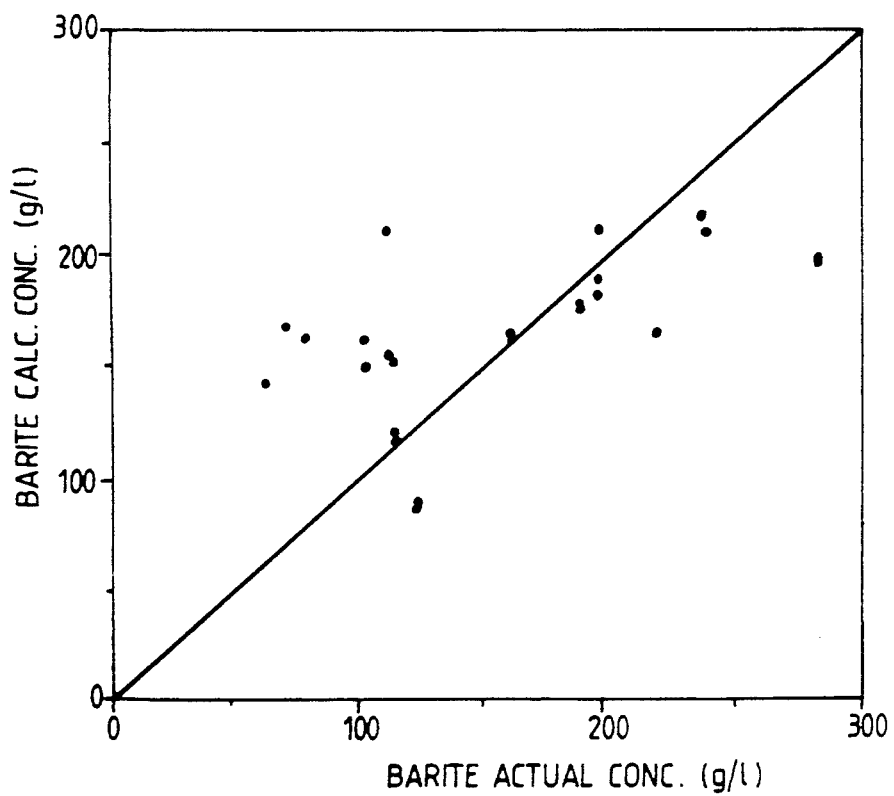
Figure 23:
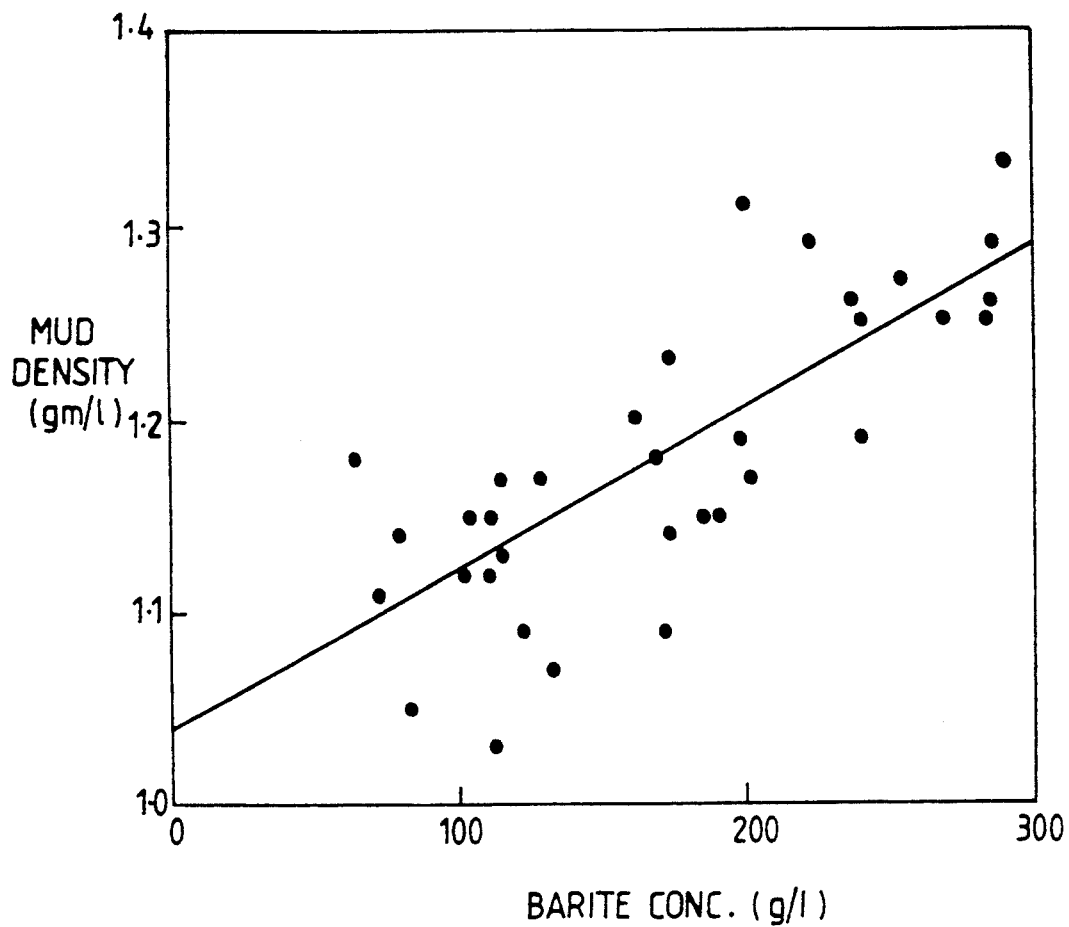
FIG. 23 Correlation between density of flowing oil-based mud and barite concentration (linear correlation coefficient of best fit straight line is 0.77)
Figure 24A:
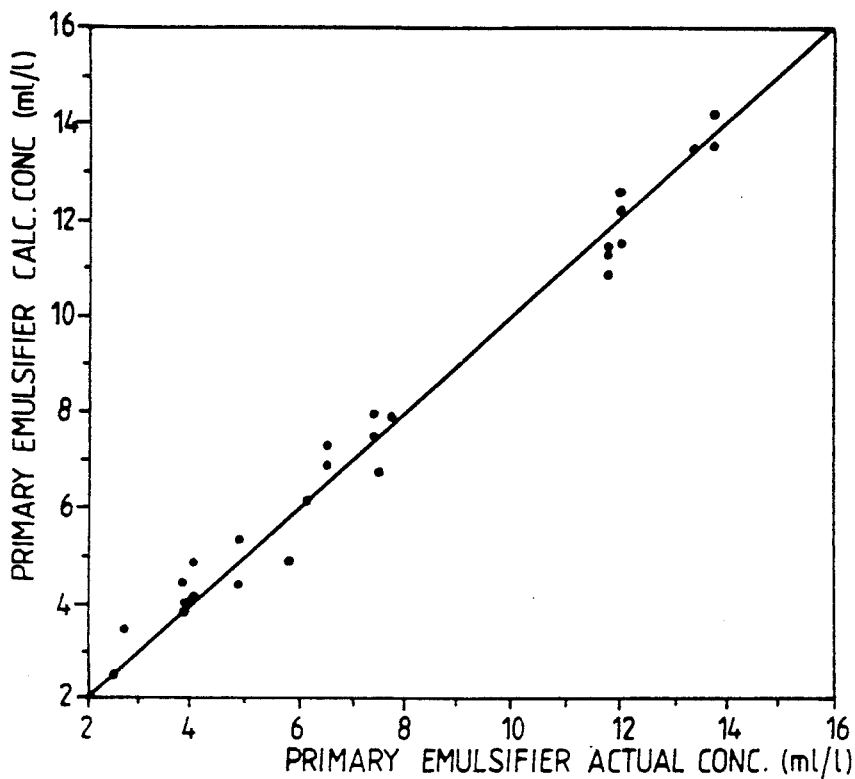
FIGS. 24A-B Prediction of primary emulsifier concentration in flowing oil-based mud: (A) calibration model using spectral and mud density data, (B) calibration model using spectral data only.
Figure 24B:
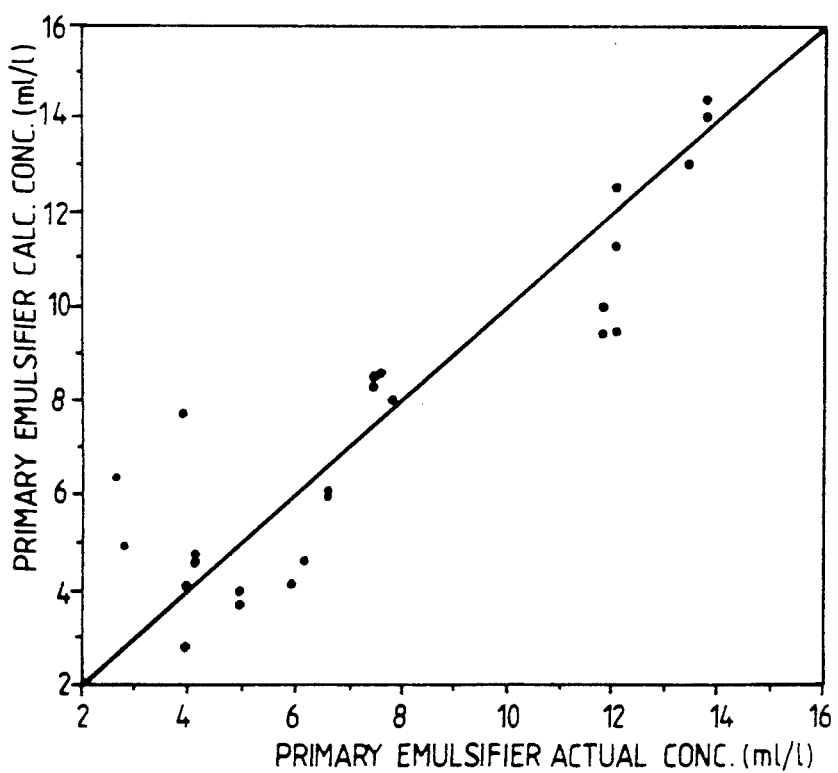

An example of each approach is now given. The first example shows the improvement to the prediction of barite and other components in a flowing oil-based mud when the spectral data are accompanied by a measurement of mud density, i.e., density is treated as spectral data. FIGS. 22A-22B show a comparison between the fit of two calibration models (A and B) to a series of validation muds; model A contains mud density and spectral data and model B contains only spectrum data. It is clear that the use of barite has significantly improved the prediction of density in the flowing oil-based muds. The use of mud density in the regression model to predict barite concentration has partly compensated for the poor fit to the spectral data caused by particle size effects. The incorporation of density data into the calibration model does not entirely replace the spectral data in predicting the barite concentration. FIG. 23 shows the relationship between barite concentration and mud density. The use of density measurements and spectral measurements in separate regression models leads to a poor prediction of barite concentration, while a model which combines both measurements results in a significantly better model than either of the separate models. The improvement in the prediction of barite concentration can result in improved predictions for other components. For example, FIGS. 24A-24B compares the fit of models A and B to the prediction of the concentration of primary emulsifier in a set of validation muds. Table 14 compares the prediction of component concentrations in models A and B for 2 test mud samples.

The second example demonstrates the prediction of the plastic viscosity of flowing oil-based mud samples from their measured infrared spectra and densities. Assuming oil-based muds behave as a Bingham plastic, then their rheology can be described by $$\tau = PV\dot{\gamma} + YP, \quad [41]$$

which relates the shear stress $\tau$ to the shear rate $\dot{\gamma}$ using the two constants PV (plastic viscosity) and YP (yield point). Parameters from other rheological models such as the Casson and Herschel-Bulkley models could also be predicted from a regression model.

Figure 25A:
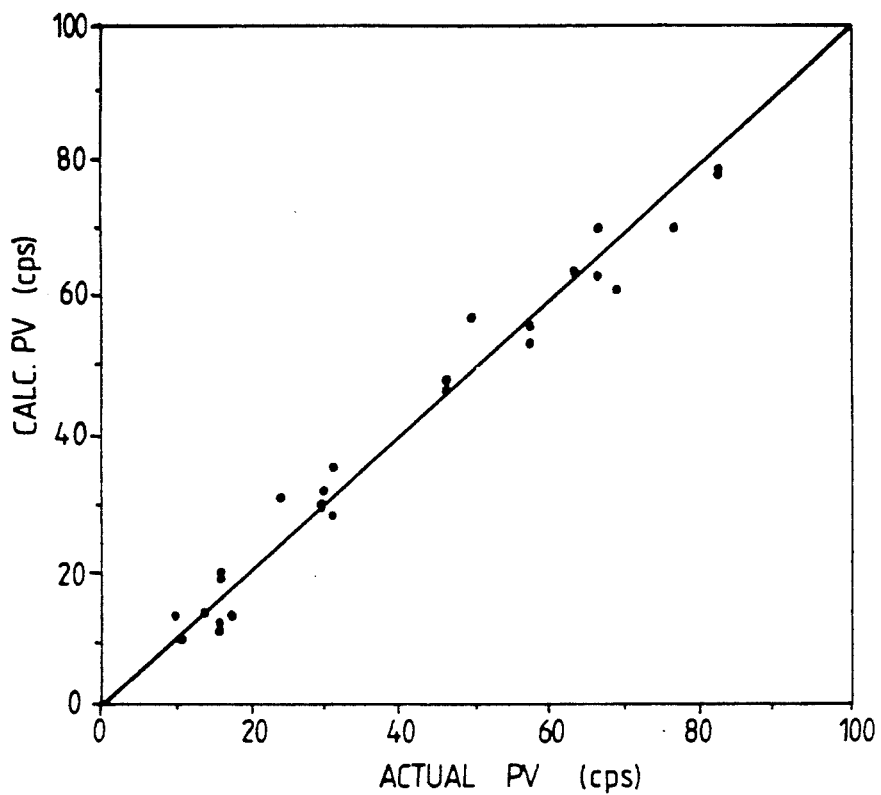
FIGS. 25A-B Prediction of plastic viscosity of flowing oil-based mud from infrared spectral measurements: (A) calibration standards, (B) validation samples.
Figure 25B:
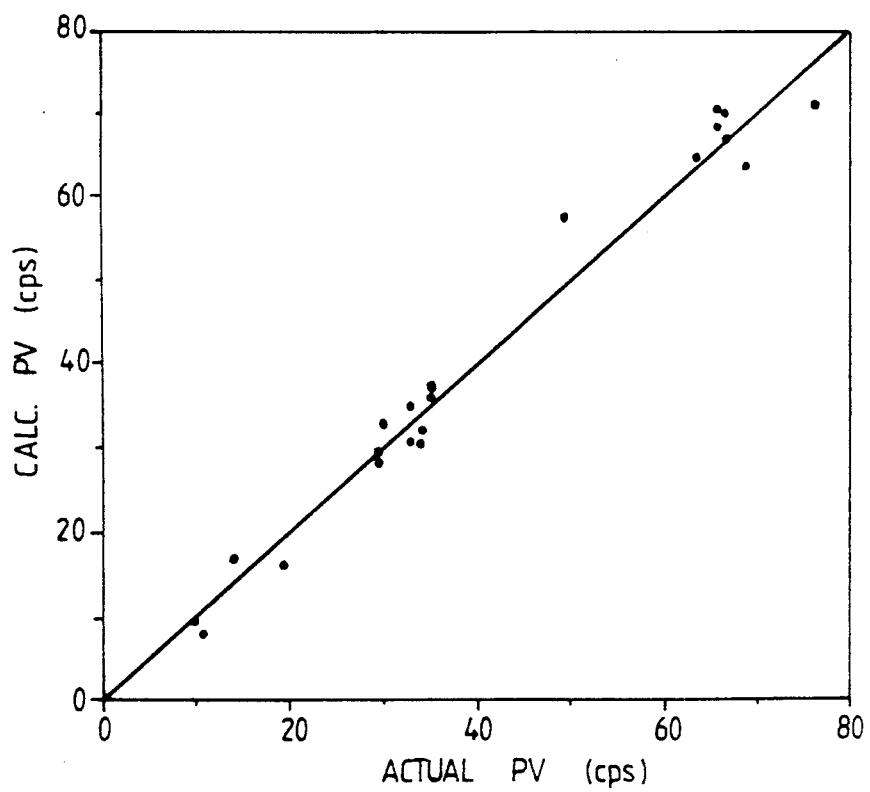
Figure 26:
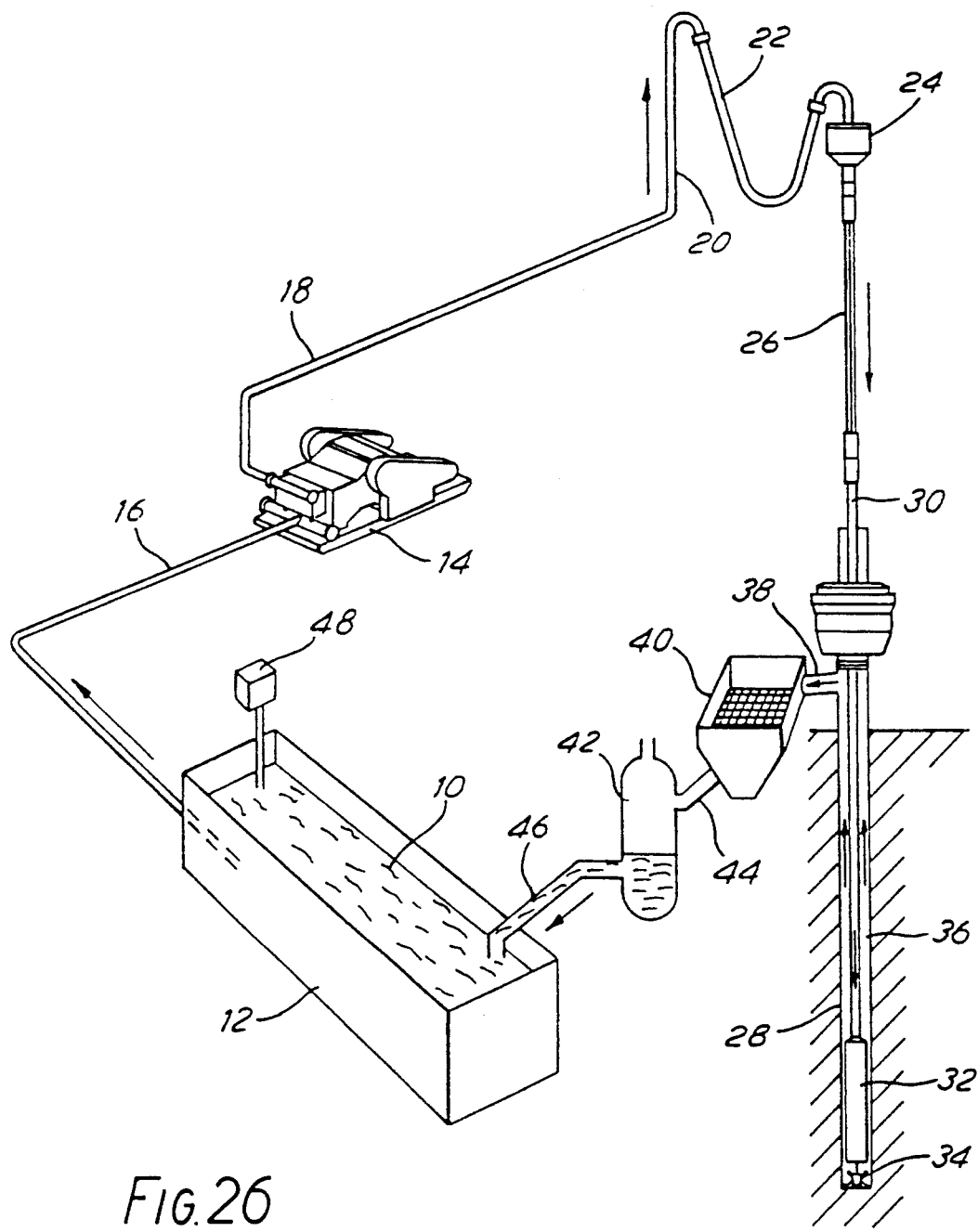
FIG. 26 Shows a diagramatic representation of a mud circulation system.

A calibration model for flowing oil-based mud is constructed with the Bingham plastic viscosity as a mud component. FIGS. 25A-25B show the fit of the calibration model to the known values of plastic viscosity in the calibration standards and a series of validation muds. The calibration model gives a generally good prediction of plastic viscosity over a wide range of values. Table 15 shows a comparison between the actual and calculated values of the components (including plastic viscosity) in two test mud samples.

Figure 20:
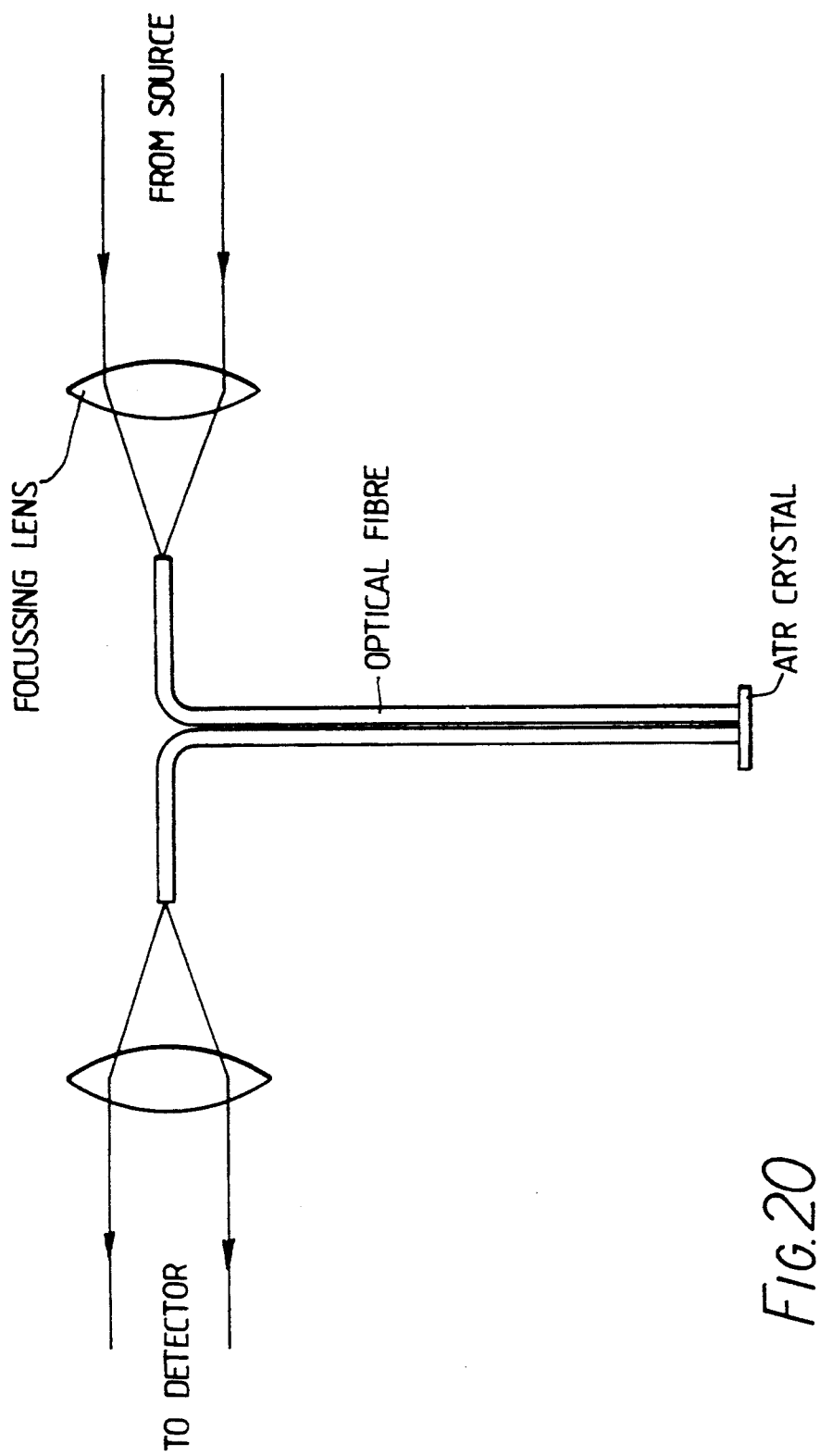
FIG. 20 Schematic of ATR crystal attached to an optical fibre for remote spectral collection.
Figure 21A:
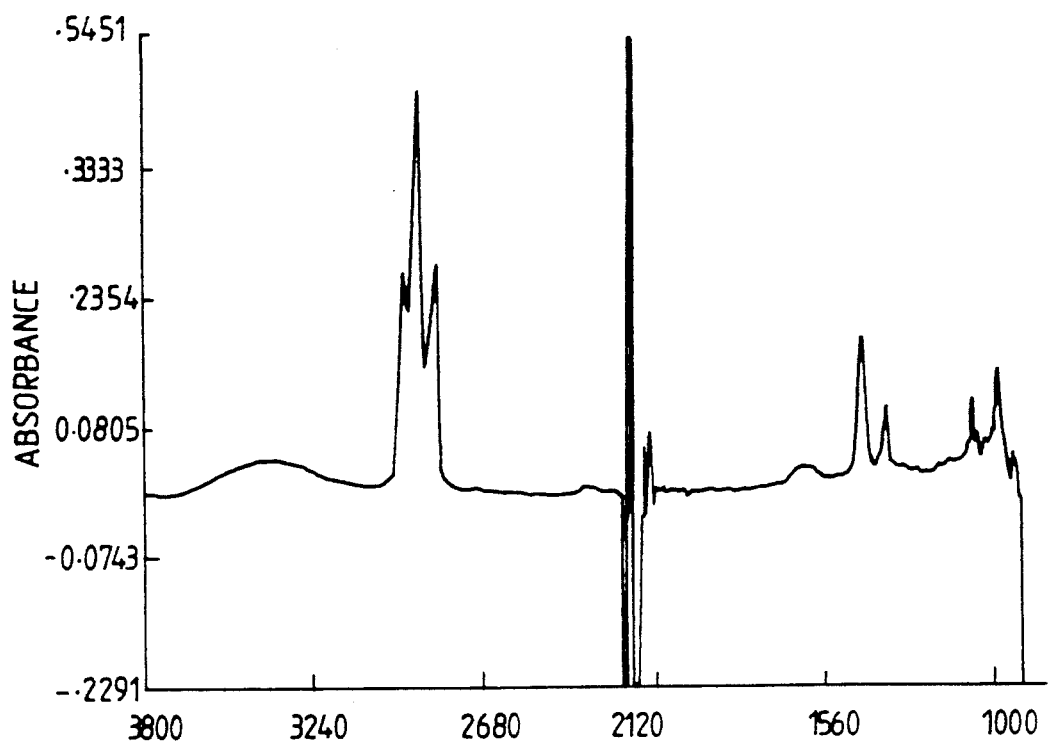
FIGS. 21A-B Comparison of static infrared spectra: (A) remote spectral collection using zinc selenide ATR crystal attached to chalcogenide glass optical fibre, (B) zinc selenide ATR crystal located within spectrometer's sample compartment.
Figure 21B:
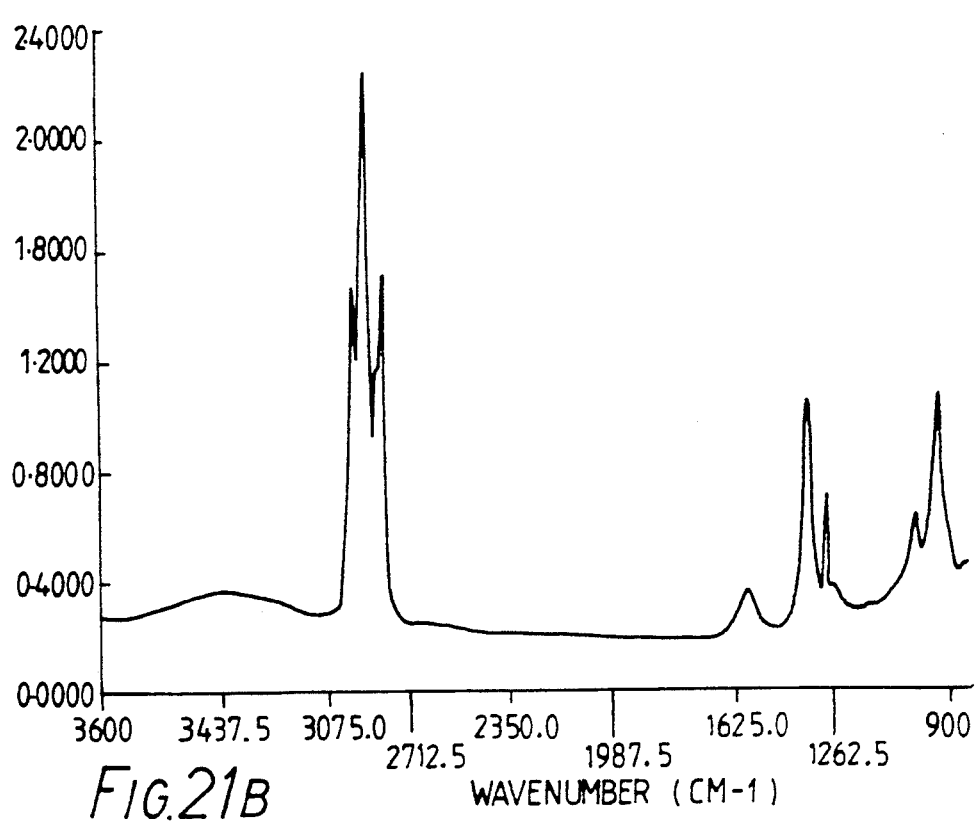

Under certain circumstances it may be preferable to collect the infrared spectrum of a mud sample at a sampling point which is remote from the infrared spectrometer. One possible solution is to use light conducting means such as an optical fibre or light pipe to conduct the infrared radiation from the source to a remote sample and back to the detector. FIG. 20 shows one possible configuration of remote sampling device which consists of a zinc selenide ATR crystal connected to the infrared spectrometer by means of a mid-infrared optical fibre; comprising of a proprietary chalcogenide glass material. FIGS. 21A-21B show the infrared spectrum of a static oil-based mud sample collected by such a configuration; the total length of the optical fibre is 4 meters, allowing a separation between spectrometer and sampling point of 2 meters. The chalcogenide glass in the optical fibre is strongly absorbing below about 1000 $cm^{-1}$ and in the region of 2300-2200 $cm^{-1}$, allowing remote spectra to be collected over most of the mid-infrared ATR spectral region. FIGS. 21A-21B also show the infrared spectrum of the oil-based mud obtained from the static ATR technique as described above. The spectra are similar and demonstrate the feasibility of using a remote sensing ATR method for mud analysis. The advantage of the remote sensor is that it allows sensors to be placed in the mud circulation system, before and after solids control equipment, such that continuous measurements can be made.

As has been stated above, solids of large particle size (typically with a mean particle diameter in excess of about 50 $\mu$m) are not detected by the ATR technique. If a quantitative analysis of solids of large particle size is required, then a wet crushing technique will need to be used (either static or on-line, depending on the ATR technique being used). This technique can be applied to the quantitative analysis of drilled cuttings and the mud products which adhere to them. The cuttings are wet crushed in the presence of a suitable liquid (e.g., water) such that their mean particle size has been reduced to below about 30 $\mu$m. The infrared spectrum of the resulting slurry is then collected using a suitable ATR cell (static or flowing) and quantification made with an appropriate calibration model. Thus by analysing the cuttings in this way together with the analysis of the mud after cuttings removal, the mud components removed can be identified and quantified.

The analysis of the present invention can be improved by using the information provided by x-ray fluorescence (XRF) analysis of the same sample. XRF analysis provides a relatively accurate estimation of components such as barite, quartz and other solids which are less accurately determined by the method according to the present invention due to particle size problems described above. By using the barite or LGS determined by XRF, as a non-spectral attribute in the PLS algorithm to analyse the IR spectrum, the contribution of these components in the spectrum can be estimated more accurately and the remaining analysis improved.

TABLE 1

| COMPONENTS IN WATER-BASED MUD CALIBRATION MODELS | |
|---|---|
| COMPONENT | CONC. RANGE (g/l) |
| CMC | 0.6–9.7 |
| PHPA | 0–5.7 |
| XC | 0–5.9 |
| Barite | 240–790 |
| Bentonite | 2–91 |

TABLE 1-continued
COMPONENTS IN WATER-BASED MUD CALIBRATION MODELS

| COMPONENT | CONC. RANGE (g/l) |
|---|---|
| Limestone | 4–47 |
| Dolomite | 2–49 |
| Quartz | 0–50 |
| OCMA | 0–43 |

TABLE 2
SUMMARY OF CALIBRATION MODEL FOR STATIC WATER-BASED MUD

| COMPONENT | CORR. COEFF. CALIB. | CORR. COEFF. VALID. |
|---|---|---|
| CMC | 0.976 | 0.976 |
| PHPA | 0.987 | 0.989 |
| XC | 0.969 | 0.972 |
| Barite | 0.917 | 0.931 |
| Bentonite | 0.983 | 0.985 |
| Limestone | 0.844 | 0.877 |
| Dolomite | 0.994 | 0.994 |
| Quartz | 0.359 | 0.228 |
| OCMA | 0.995 | 0.991 |

TABLE 3
PREDICTION OF CONCENTRATION: STATIC WATER-BASED MUD

| TEST MUD | COMPONENT | ACT. CONC (g/l) | CALC. CONC. (g/l) | % DIFF. |
|---|---|---|---|---|
| 1 | CMC | 7.58 | 7.35 | 3.0 |
|   | PHPA | 2.61 | 2.05 | −27.3 |
|   | XC | 0.60 | 0.70 | 16.7 |
|   | Barite | 429.80 | 447.50 | 4.1 |
|   | Bentonite | 17.16 | 20.50 | 19.5 |
|   | Limestone | 16.78 | 20.50 | 22.2 |
|   | Dolomite | 12.70 | 15.20 | 19.7 |
|   | Quartz | 27.33 | 25.25 | −7.6 |
|   | OCMA | 16.43 | 16.50 | 0.4 |
| 2 | CMC | 8.37 | 6.35 | −24.1 |
|   | PHPA | 2.84 | 2.65 | −6.7 |
|   | XC | 2.26 | 2.50 | 9.6 |
|   | Barite | 279.10 | 305.70 | 9.5 |
|   | Bentonite | 64.40 | 61.40 | −4.7 |
|   | Limestone | 35.33 | 35.50 | 0.5 |
|   | Dolomite | 8.52 | 8.55 | 0.1 |
|   | Quartz | 19.11 | 2.90 | 85.0 |
|   | OCMA | 8.26 | 10.40 | 25.9 |

TABLE 4
MEAN PARTICLE SIZE OF SOLIDS IN WATER-BASED MUD MODEL

| COMPONENT | CALIB. CORR. | VALID. CORR. | $d_m$ (μm) |
|---|---|---|---|
| Barite | −0.917 | 0.931 | 35.2 |
| Bentonite | 0.983 | 0.985 | 6.8 |
| Limestone | 0.844 | 0.877 | 27.6 |
| Dolomite | 0.994 | 0.994 | 9.3 |
| Quartz | 0.359 | 0.228 | 158.0 |
| OCMA | 0.995 | 0.991 | 14.4 |

TABLE 5
SUMMARY OF CALIBRATION MODEL FOR FLOWING WATER-BASED MUD

| COMPONENT | CORR. COEFF. CALIB. | CORR. COEFF. VALID. |
|---|---|---|
| CMC | 0.993 | 0.991 |
| PHPA | 0.992 | 0.992 |
| XC | 0.780 | 0.684 |
| Barite | 0.992 | 0.992 |
| Bentonite | 0.996 | 0.995 |
| Limestone | 0.927 | 0.937 |
| Dolomite | 0.962 | 0.962 |
| Quartz | 0.116 | 0.014 |
| OCMA | 0.975 | 0.983 |

TABLE 6
PREDICTION OF CONCENTRATION: FLOWING WATER-BASED MUD

| TEST MUD | COMPONENT | ACT. CONC. (g/l) | CALC. CONC. (g/l) | % DIFF. |
|---|---|---|---|---|
| 1 | CMC | 1.19 | 1.19 | 0 |
|   | PHPA | 2.71 | 2.69 | −0.7 |
|   | XC | 1.93 | 2.01 | 4.1 |
|   | Barite | 254.90 | 237.60 | −6.8 |
|   | Bentonite | 5.84 | 4.71 | −19.3 |
|   | Limestone | 20.39 | 22.28 | 9.3 |
|   | Dolomite | 44.58 | 42.63 | −4.4 |
|   | Quartz | 31.47 | 20.41 | −35.1 |
|   | OCMA | 26.04 | 28.42 | 9.1 |
| 2 | CMC | 0.31 | 0.25 | −19.4 |
|   | PHPA | 2.86 | 2.73 | −4.5 |
|   | XC | 1.51 | 1.71 | 13.2 |
|   | Barite | 555.20 | 564.60 | 1.7 |
|   | Bentonite | 28.02 | 28.40 | 1.4 |
|   | Limestone | 31.04 | 28.76 | −7.3 |
|   | Dolomite | 8.88 | 8.65 | −2.6 |
|   | Quartz | 14.09 | 24.81 | 76.0 |
|   | OCMA | 24.18 | 23.11 | −4.4 |

TABLE 7
SUMMARY OF CALIBRATION MODEL FOR POLYMERS IN MUD FILTRATE

| COMPONENT | CORR. COEFF. CALIB. | CORR. COEFF. VALID. |
|---|---|---|
| CMC | 0.998 | 0.991 |
| XC | 0.997 | 0.992 |
| PHPA | 0.998 | 0.950 |
| Guar Gum | 0.999 | 0.988 |

TABLE 8
PREDICTION OF CONCENTRATION: POLYMERS IN MUD FILTRATE

| TEST MUD | COMPONENT | ACT. CONC. (g/l) | CALC. CONC. (g/l) | % DIFF. |
|---|---|---|---|---|
| 1 | CMC | 7.42 | 7.90 | 6.5 |
|   | XC | 3.76 | 4.00 | 6.4 |
|   | PHPA | 5.41 | 6.30 | 16.5 |
|   | Guar Gum | 2.91 | 2.60 | −10.7 |
| 2 | CMC | 3.40 | 3.20 | −5.9 |
|   | XC | 4.86 | 5.20 | 7.0 |
|   | PHPA | 5.66 | 6.00 | 5.7 |
|   | Guar Gum | 4.32 | 4.40 | 1.9 |

TABLE 9
COMPONENTS IN OIL-BASED MUD CALIBRATION MODELS

| COMPONENT | CONC. RANGE | UNITS |
|---|---|---|
| Base Oil | 370–780 | ml/l |
| Primary Emulsifier | 2.6–15.7 | ml/l |
| Secondary Emulsifier | 3.0–17.1 | ml/l |
| Water | 94–485 | ml/l |
| Calcium Chloride | 0.5–5.2 | mol/l |
| Water Activity | 0.474–0.974 | — |
| Barite | 62–286 | g/l |
| Organophilic Clay | 3.0–19.2 | g/l |
| Limestone | 0–143 | g/l |

TABLE 9-continued
COMPONENTS IN OIL-BASED MUD CALIBRATION MODELS

| COMPONENT | CONC. RANGE | UNITS |
|---|---|---|
| OCMA | 19–148 | g/l |

TABLE 10
SUMMARY OF CALIBRATION MODEL FOR STATIC OIL-BASED MUD

| COMPONENT | CORR. COEFF. CALIB. | CORR. COEFF. VALID. |
|---|---|---|
| Base Oil | 0.944 | 0.979 |
| Primary Emulsifier | 0.989 | 0.951 |
| Secondary Emulsifier | 0.898 | 0.883 |
| Water | 0.935 | 0.968 |
| Water Activity | 0.867 | 0.947 |
| Barite | 0.971 | 0.976 |
| Organophilic Clay | 0.982 | 0.955 |
| Limestone | 0.783 | 0.773 |
| OCMA | 0.975 | 0.979 |

TABLE 11
PREDICTION OF CONCENTRATION: STATIC OIL-BASED MUD

| TEST MUD | COMPONENT | ACT. CONC.[1] | CALC. CONC. | % DIFF. |
|---|---|---|---|---|
| 1 | Base Oil | 477.60 | 494.90 | 3.6 |
|   | Primary Emulsifier | 4.78 | 4.00 | −16.3 |
|   | Secondary Emulsifier | 13.41 | 10.70 | −20.2 |
|   | Water | 339.20 | 321.50 | −5.2 |
|   | Water Activity | 0.85 | 0.84 | −1.2 |
|   | Barite | 127.30 | 148.50 | 16.6 |
|   | Organophilic Clay | 14.75 | 14.20 | −3.7 |
|   | Limestone | 71.05 | 57.40 | −19.2 |
|   | OCMA | 70.99 | 91.10 | 28.3 |
| 2 | Base Oil | 629.20 | 640.00 | 1.7 |
|   | Primary Emulsifier | 10.45 | 7.25 | −30.6 |
|   | Secondary Emulsifier | 8.29 | 10.14 | 22.3 |
|   | Water | 184.50 | 168.80 | −8.5 |
|   | Water Activity | 0.79 | 0.82 | 3.8 |
|   | Barite | 199.80 | 203.70 | 2.0 |
|   | Organophilic Clay | 7.40 | 8.60 | −16.2 |
|   | Limestone | 3.42 | 12.70 | 271.3 |
|   | OCMA | 139.70 | 123.60 | −11.5 |

[1]Units for components as shown in Table 6

TABLE 12
SUMMARY OF CALIBRATION MODEL FOR FLOWING OIL-BASED MUD

| COMPONENT | CORR. COEFF. CALIB. | CORR. COEFF. VALID. |
|---|---|---|
| Base Oil | 0.992 | 0.990 |
| Primary Emulsifier | 0.993 | 0.990 |
| Secondary Emulsifier | 0.996 | 0.997 |
| Water | 0.999 | 0.999 |
| Water Activity | 0.935 | 0.926 |
| Barite | 0.971 | 0.960 |
| Organophilic Clay | 0.962 | 0.963 |
| Limestone | 0.948 | 0.939 |
| OCMA | 0.942 | 0.942 |

TABLE 13
PREDICTION OF CONCENTRATION: FLOWING OIL-BASED MUD

| TEST MUD | COMPONENT | ACT. CONC.[1] | CALC. CONC. | % DIFF. |
|---|---|---|---|---|
| 1 | Base Oil | 477.60 | 493.20 | 3.3 |
|   | Primary Emulsifier | 4.78 | 7.30 | 52.7 |
|   | Secondary Emulsifier | 13.41 | 11.95 | −10.9 |
|   | Water | 339.20 | 331.50 | −2.3 |
|   | Water Activity | 0.85 | 0.90 | 5.9 |
|   | Barite | 127.30 | 117.10 | −8.1 |
|   | Organophilic Clay | 14.75 | 14.35 | −2.7 |
|   | Limestone | 71.05 | 56.60 | −20.3 |
|   | OCMA | 70.99 | 84.75 | 19.4 |
| 2 | Base Oil | 629.20 | 643.60 | 2.3 |
|   | Primary Emulsifier | 10.45 | 7.10 | −32.1 |
|   | Secondary Emulsifier | 8.29 | 11.46 | 38.2 |
|   | Water | 184.50 | 163.80 | −11.2 |
|   | Water Activity | 0.79 | 0.75 | −5.1 |
|   | Barite | 199.80 | 204.20 | 2.2 |
|   | Organophilic Clay | 7.40 | 9.90 | 33.8 |
|   | Limestone | 3.42 | 14.00 | 309.0 |
|   | OCMA | 139.70 | 140.60 | 0.6 |

[1]Units for components as shown in Table 6

TABLE 14
PREDICTION OF CONCENTRATION: FLOWING OIL-BASED MUD WITH AND WITHOUT MUD DENSITY

| TEST MUD | COMPONENT | ACT. CONC.[1] | CALC. CONC. (A) | CALC. CONC. (B) |
|---|---|---|---|---|
| 1 | Base Oil | 505.00 | 492.80 | 533.60 |
|   | Primary Emulsifier | 3.91 | 3.94 | 3.33 |
|   | Secondary Emulsifier | 14.74 | 14.77 | 14.77 |
|   | Water | 311.60 | 311.80 | 310.55 |
|   | Water Activity | 0.85 | 0.86 | 0.84 |
|   | Barite | 113.70 | 117.70 | 118.70 |
|   | Organophilic Clay | 7.54 | 7.75 | 6.40 |
|   | Limestone | 119.80 | 116.30 | 121.80 |
|   | OCMA | 46.41 | 48.07 | 45.98 |
| 2 | Base Oil | 521.60 | 532.20 | 533.60 |
|   | Primary Emulsifier | 4.90 | 4.87 | 3.71 |
|   | Secondary Emulsifier | 11.67 | 11.06 | 10.98 |
|   | Water | 258.90 | 259.30 | 263.70 |
|   | Water Activity | 0.80 | 0.84 | 0.83 |
|   | Barite | 235.40 | 243.30 | 215.80 |
|   | Organophilic Clay | 15.26 | 15.08 | 14.23 |
|   | Limestone | 6.85 | 16.98 | 10.61 |
|   | OCMA | 147.90 | 125.60 | 123.50 |

[1]Units for components as shown in Table 6

TABLE 15
PREDICTION OF CONCENTRATION AND PLASTIC VISCOSITY: FLOWING OIL-BASED MUD

| TEST MUD | COMPONENT | ACT. CONC.[1] | CALC. CONC. | % DIFF. |
|---|---|---|---|---|
| 1 | Base Oil | 475.10 | 464.90 | −2.1 |
|   | Primary Emulsifier | 4.08 | 5.93 | 45.3 |
|   | Secondary Emulsifier | 3.51 | 3.54 | 0.9 |
|   | Water | 346.10 | 347.20 | 0.3 |
|   | Water Activity | 0.85 | 0.84 | −1.2 |
|   | Barite | 161.00 | 158.10 | −1.8 |
|   | Organophilic Clay | 19.50 | 20.75 | 6.4 |
|   | Limestone | 99.88 | 100.60 | 0.7 |
|   | OCMA | 29.88 | 40.45 | 34.5 |
|   | Plastic Viscosity[2] | 65.00 | 69.30 | 6.6 |
| 2 | Base Oil | 629.20 | 643.60 | 2.3 |
|   | Primary Emulsifier | 10.45 | 7.10 | −32.1 |
|   | Secondary Emulsifier | 8.29 | 11.46 | 38.2 |
|   | Water | 184.50 | 163.80 | −11.2 |
|   | Water Activity | 0.79 | 0.75 | −5.1 |
|   | Barite | 199.80 | 204.20 | 2.2 |
|   | Organophilic Clay | 7.40 | 9.90 | 33.8 |
|   | Limestone | 3.42 | 14.00 | 309.0 |
|   | OCMA | 139.70 | 140.60 | 0.6 |
|   | Plastic Viscosity | 33.00 | 32.80 | −0.6 |

[1]Units for components as shown in Table 6
[2]Plastic viscosity reported in units of centipoise

We claim:

1. A method of quantitative analysis of a drilling mud comprising solid and liquid components which are dispersed or dissolved in a carrier liquid, the method comprising:
   a) taking a sample of the drilling mud, said sample including said carrier liquid;
   b) recording the infra-red spectrum of said sample using an attenuated total reflectance technique; and
   c) comparing said spectrum with a model in which the contribution of the components of the drilling mud to its infra-red spectrum is predicted in order to determine the composition of said sample and hence the drilling mud.

2. A method as claimed in claim 1, further comprising subjecting said sample to a crushing operation to reduce the size of solid components contained in said sample.

3. A method as claimed in claim 2, wherein the particle size is reduced to less than about 30 microns.

4. A method as claimed in claim 1, comprising taking said sample from circulating drilling mud in a circulation system at a rig-site.

5. A method as claimed in claim 4, wherein the step of taking said sample of said drilling mud comprises flowing at least a part of said circulating drilling mud through or past a measurement station and measuring the infra-red spectrum of the flowing drilling mud.

6. A method as claimed in claim 4, wherein the step of taking a sample comprises removing solids from the circulating drilling mud; crushing said solids to reduce the particle size thereof; and suspending the crushed solids in said carrier liquid.

7. A method as claimed in claim 6, wherein said crushing step comprises crushing said solids in the presence of said carrier liquid.

8. A method as claimed in claim 6, wherein the analysis of the removed solids is combined with an analysis of said drilling mud after said solids have been removed to provide a quantitative determination of the whole drilling mud.

9. A method as claimed in claim 1, wherein the model relates the infra-red spectrum to at least one physical property of the drilling mud.

10. A method as claimed in claim 9, wherein said at least one physical property is selected from the group consisting of density, fluid loss, plastic viscosity and yield point.

11. A method as claimed in claim 1, wherein said calibration model includes a parameter relating to the shear history of the sample.

12. A method of quantitative analysis of a drilling mud comprising solid and liquid components which are dispersed or dissolved in a carrier liquid, the method comprising:
   a) taking a sample of said drilling mud at a sampling point so as to include said carrier liquid;
   b) recording the infra-red spectrum of said sample using an attenuated total reflectance technique at a detector which is remote from said sampling point and connected thereto by light conducting means; and
   c) comparing said spectrum with a model in which the contribution of the components of the drilling mud to its infra-red spectrum is predicted in order to determine the composition of said sample and hence the drilling mud.

* * * * *